United States Patent
Feige et al.

(10) Patent No.: US 10,828,347 B2
(45) Date of Patent: Nov. 10, 2020

(54) METHODS FOR TREATING SARCOPENIA AND MUSCLE INJURY

(71) Applicant: NESTEC S.A., Vevey (CH)

(72) Inventors: Jerome Feige, Crissier (CH); Laura Lukjanenko, Lausanne (CH)

(73) Assignee: Societe des Produits Nestle S.A., Vevey (CH)

( * ) Notice: Subject to any disclaimer, the term of this patent is extended or adjusted under 35 U.S.C. 154(b) by 31 days.

(21) Appl. No.: 16/304,790

(22) PCT Filed: Jun. 1, 2017

(86) PCT No.: PCT/EP2017/063238
§ 371 (c)(1),
(2) Date: Nov. 27, 2018

(87) PCT Pub. No.: WO2017/207678
PCT Pub. Date: Dec. 7, 2017

(65) Prior Publication Data
US 2019/0255149 A1    Aug. 22, 2019

(30) Foreign Application Priority Data

Jun. 2, 2016 (EP) .................................. 16172719

(51) Int. Cl.
| | | |
|---|---|---|
| *A61K 38/18* | (2006.01) |
| *A61P 21/00* | (2006.01) |
| *A61K 38/16* | (2006.01) |
| *G01N 33/74* | (2006.01) |
| *G01N 33/68* | (2006.01) |

(52) U.S. Cl.
CPC .............. *A61K 38/18* (2013.01); *A61K 38/16* (2013.01); *A61P 21/00* (2018.01); *G01N 33/6893* (2013.01); *G01N 33/74* (2013.01); *G01N 2333/475* (2013.01); *G01N 2500/10* (2013.01); *G01N 2800/10* (2013.01)

(58) Field of Classification Search
CPC .......... A61K 38/18; A61K 38/16; A61P 21/00
See application file for complete search history.

(56) References Cited

FOREIGN PATENT DOCUMENTS

| WO | 2005025603 | 3/2005 |
| WO | 2015148923 | 10/2015 |

OTHER PUBLICATIONS

Maiese, Kenneth "Novel applications of trophic factors, Wnt and WISP for neuronal repair and regeneration in metabolic disease" Neural Regeneration Research, Apr. 2015, vol. 10, No. 4, pp. 518-528.
Stephens et al. "A functional analysis of Wnt inducible signalling pathway protein-1 (WISP-1/CCN4)" J. Cell Commun. Signal, 2015, vol. 9, pp. 63-72.
Liu et al. "CCN4 Regulates Vascular Smooth Muscle Cell Migration and Proliferation" Molecules and Cells, Aug. 31, 2013, vol. 36, pp. 112-118.
Schlegelmilch et al. "WISP 1 is an important survival factor in human mesenchymal stromal cells" Gene, 2014, vol. 551, pp. 243-254.

*Primary Examiner* — Daniel C Gamett
(74) *Attorney, Agent, or Firm* — K&L Gates LLP

(57) ABSTRACT

Wnt-inducible signalling protein 1 (WISP1) or a fragment or variant thereof for use in maintaining or increasing muscle function and/or mass in a subject, and/or substantially preventing or reducing muscle wasting in a subject.

12 Claims, 8 Drawing Sheets

Specification includes a Sequence Listing.

SEQUENCE LISTING

<160> NUMBER OF SEQ ID NOS: 10

<210> SEQ ID NO 1
<211> LENGTH: 367
<212> TYPE: PRT
<213> ORGANISM: Homo sapiens

<400> SEQUENCE: 1

```
Met Arg Trp Phe Leu Pro Trp Thr Leu Ala Ala Val Thr Ala Ala Ala
1               5                   10                  15

Ala Ser Thr Val Leu Ala Thr Ala Leu Ser Pro Ala Pro Thr Thr Met
            20                  25                  30

Asp Phe Thr Pro Ala Pro Leu Glu Asp Thr Ser Ser Arg Pro Gln Phe
        35                  40                  45

Cys Lys Trp Pro Cys Glu Cys Pro Ser Pro Pro Arg Cys Pro Leu
    50                  55                  60

Gly Val Ser Leu Ile Thr Asp Gly Cys Glu Cys Cys Lys Met Cys Ala
65                  70                  75                  80

Gln Gln Leu Gly Asp Asn Cys Thr Glu Ala Ala Ile Cys Asp Pro His
                85                  90                  95

Arg Gly Leu Tyr Cys Asp Tyr Ser Gly Asp Arg Pro Arg Tyr Ala Ile
            100                 105                 110

Gly Val Cys Ala Gln Val Val Gly Val Gly Cys Val Leu Asp Gly Val
        115                 120                 125

Arg Tyr Asn Asn Gly Gln Ser Phe Gln Pro Asn Cys Lys Tyr Asn Cys
    130                 135                 140

Thr Cys Ile Asp Gly Ala Val Gly Cys Thr Pro Leu Cys Leu Arg Val
145                 150                 155                 160

Arg Pro Pro Arg Leu Trp Cys Pro His Pro Arg Arg Val Ser Ile Pro
                165                 170                 175

Gly His Cys Cys Glu Gln Trp Val Cys Glu Asp Ala Lys Arg Pro
            180                 185                 190

Arg Lys Thr Ala Pro Arg Asp Thr Gly Ala Phe Asp Ala Val Gly Glu
        195                 200                 205

Val Glu Ala Trp His Arg Asn Cys Ile Ala Tyr Thr Ser Pro Trp Ser
210                 215                 220

Pro Cys Ser Thr Ser Cys Gly Leu Gly Val Ser Thr Arg Ile Ser Asn
225                 230                 235                 240

Val Asn Ala Gln Cys Trp Pro Glu Gln Glu Ser Arg Leu Cys Asn Leu
                245                 250                 255

Arg Pro Cys Asp Val Asp Ile His Thr Leu Ile Lys Ala Gly Lys Lys
            260                 265                 270

Cys Leu Ala Val Tyr Gln Pro Glu Ala Ser Met Asn Phe Thr Leu Ala
        275                 280                 285

Gly Cys Ile Ser Thr Arg Ser Tyr Gln Pro Lys Tyr Cys Gly Val Cys
    290                 295                 300

Met Asp Asn Arg Cys Cys Ile Pro Tyr Lys Ser Lys Thr Ile Asp Val
305                 310                 315                 320

Ser Phe Gln Cys Pro Asp Gly Leu Gly Phe Ser Arg Gln Val Leu Trp
                325                 330                 335

Ile Asn Ala Cys Phe Cys Asn Leu Ser Cys Arg Asn Pro Asn Asp Ile
            340                 345                 350

Phe Ala Asp Leu Glu Ser Tyr Pro Asp Phe Ser Glu Ile Ala Asn
        355                 360                 365
```

<210> SEQ ID NO 2
<211> LENGTH: 2830
<212> TYPE: DNA
<213> ORGANISM: Homo sapiens
<220> FEATURE:
<221> NAME/KEY: source
<222> LOCATION: 1..2830
<223> OTHER INFORMATION: /mol_type="unassigned DNA"
       /organism="Homo sapiens"

<400> SEQUENCE: 2

| | | | | | |
|---|---|---|---|---|---|
| cccacgcgtc | cgctgggccc | agctcccccg | agaggtggtc | ggatcctctg | ggctgctcgg | 60 |
| tcgatgcctg | tgccactgac | gtccaggcat | gaggtggttc | ctgccctgga | cgctggcagc | 120 |
| agtgacagca | gcagccgcca | gcaccgtcct | ggccacggcc | ctctctccag | ccccctacgac | 180 |
| catggacttt | actccagctc | cactggagga | cacctcctca | cgcccccaat | tctgcaagtg | 240 |
| gccatgtgag | tgcccgccat | ccccacccccg | ctgcccgctg | ggggtcagcc | tcatcacaga | 300 |
| tggctgtgag | tgctgtaaga | tgtgcgctca | gcagcttggg | gacaactgca | cggaggctgc | 360 |
| catctgtgac | ccccaccggg | gcctctactg | tgactacagc | ggggaccgcc | cgaggtacgc | 420 |
| aataggagtg | tgtgcacagg | tggtcggtgt | gggctgcgtc | ctggatgggg | tgcgctacaa | 480 |
| caacggccag | tccttccagc | ctaactgcaa | gtacaactgc | acgtgcatcg | acggcgcggt | 540 |
| gggctgcaca | ccactgtgcc | tccgagtgcg | ccccccgcgt | ctctggtgcc | ccacccgcg | 600 |
| gcgcgtgagc | atacctggcc | actgctgtga | gcagtgggta | tgtgaggacg | acgccaagag | 660 |
| gccacgcaag | accgcacccc | gtgacacagg | agccttcgat | gctgtgggtg | aggtggaggc | 720 |
| atggcacagg | aactgcatag | cctacacaag | cccctggagc | ccttgctcca | ccagctgcgg | 780 |
| cctggggggtc | tccactcgga | tctccaatgt | taacgcccag | tgctggcctg | agcaagagag | 840 |
| ccgcctctgc | aacttgcggc | catgcgatgt | ggacatccat | acactcatta | aggcagggaa | 900 |
| gaagtgtctg | gctgtgtacc | agccagaggc | atccatgaac | ttcacacttg | cgggctgcat | 960 |
| cagcacacgc | tcctatcaac | ccaagtactg | tggagtttgc | atggacaata | ggtgctgcat | 1020 |
| cccctacaag | tctaagacta | tcgacgtgtc | cttccagtgt | cctgatgggc | ttggcttctc | 1080 |
| ccgccaggtc | ctatggatta | atgcctgctt | ctgtaacctg | agctgtagga | atcccaatga | 1140 |
| catctttgct | gacttggaat | cctaccctga | cttctcagaa | attgccaact | aggcaggcac | 1200 |
| aaatcttggg | tcttggggac | taacccaatg | cctgtgaagc | agtcagccct | tatggccaat | 1260 |
| aacttttcac | caatgagcct | tagttaccct | gatctggacc | cttggcctcc | atttctgtct | 1320 |
| ctaaccattc | aaatgacgcc | tgatggtgct | gctcaggccc | atgctatgag | ttttctcctt | 1380 |
| gatatcattc | agcatctact | ctaaagaaaa | atgcctgtct | ctagctgttc | tggactacac | 1440 |
| ccaagcctga | tccagccttt | ccaagtcact | agaagtcctg | ctggatcttg | cctaaatccc | 1500 |
| aagaaatgga | atcaggtaga | cttttaatat | cactaatttc | ttctttagat | gccaaaccac | 1560 |
| aagactcttt | gggtccattc | agatgaatag | atggaatttg | gaacaataga | ataatctatt | 1620 |
| atttggagcc | tgccaagagg | tactgtaatg | ggtaattctg | acgtcagcgc | accaaaacta | 1680 |
| tcctgattcc | aaatatgtat | gcacctcaag | gtcatcaaac | atttgccaag | tgagttgaat | 1740 |
| agttgcttaa | ttttgattt | taatggaaag | ttgtatccat | taacctgggc | attgttgagg | 1800 |
| ttaagtttct | cttcaccccct | acactgtgaa | gggtacagat | taggtttgtc | ccagtcagaa | 1860 |
| ataaatttg | ataaacattc | ctgttgatgg | gaaaagcccc | cagttaatac | tccagagaca | 1920 |
| gggaaaggtc | agcccatttc | agaaggacca | attgactctc | acactgaatc | agctgctgac | 1980 |

| | |
|---|---|
| tggcagggct ttgggcagtt ggccaggctc ttccttgaat cttctcccctt gtcctgcttg | 2040 |
| ggttcatagg aattggtaag gcctctggac tggcctgtct ggcccctgag agtggtgccc | 2100 |
| tggaacactc ctctactctt acagagcctt gagagaccca gctgcagacc atgccagacc | 2160 |
| cactgaaatg accaagacag gttcaggtag gggtgtgggt caaaccaaga agtgggtgcc | 2220 |
| cttggtagca gcctggggtg acctctagag ctggaggctg tgggactcca ggggcccccg | 2280 |
| tgttcaggac acatctattg cagagactca tttcacagcc tttcgttctg ctgaccaaat | 2340 |
| ggccagtttt ctggtaggaa gatggaggtt taccagttgt ttagaaacag aaatagactt | 2400 |
| aataaaggtt taaagctgaa gaggttgaag ctaaaaggaa aaggttgttg ttaatgaata | 2460 |
| tcaggctatt atttattgta ttaggaaaat ataatattta ctgttagaat tcttttattt | 2520 |
| agggcctttt ctgtgccaga cattgctctc agtgctttgc atgtattagc tcactgaatc | 2580 |
| ttcacgacaa tgttgagaag ttcccattat tatttctgtt cttacaaatg tgaaacggaa | 2640 |
| gctcatagag gtgagaaaac tcaaccagag tcacccagtt ggtgactggg aaagttagga | 2700 |
| ttcagatcga aattggactg tctttataac ccatattttc cccctgtttt tagagcttcc | 2760 |
| aaatgtgtca gaataggaaa acattgcaat aaatggcttg attttttaaa aaaaaaaaa | 2820 |
| aaaaaaaaaa | 2830 |

```
<210> SEQ ID NO 3
<211> LENGTH: 367
<212> TYPE: PRT
<213> ORGANISM: Mus musculus

<400> SEQUENCE: 3
```

Met Arg Trp Leu Leu Pro Trp Thr Leu Ala Ala Val Ala Val Leu Arg
1               5                   10                  15

Val Gly Asn Ile Leu Ala Thr Ala Leu Ser Pro Thr Pro Thr Thr Met
            20                  25                  30

Thr Phe Thr Pro Ala Pro Leu Glu Glu Thr Thr Thr Arg Pro Glu Phe
        35                  40                  45

Cys Lys Trp Pro Cys Glu Cys Pro Gln Ser Pro Pro Arg Cys Pro Leu
    50                  55                  60

Gly Val Ser Leu Ile Thr Asp Gly Cys Glu Cys Cys Lys Ile Cys Ala
65                  70                  75                  80

Gln Gln Leu Gly Asp Asn Cys Thr Glu Ala Ala Ile Cys Asp Pro His
                85                  90                  95

Arg Gly Leu Tyr Cys Asp Tyr Ser Gly Asp Arg Pro Arg Tyr Ala Ile
            100                 105                 110

Gly Val Cys Ala Gln Val Val Gly Val Gly Cys Val Leu Asp Gly Val
        115                 120                 125

Arg Tyr Thr Asn Gly Glu Ser Phe Gln Pro Asn Cys Arg Tyr Asn Cys
    130                 135                 140

Thr Cys Ile Asp Gly Thr Val Gly Cys Thr Pro Leu Cys Leu Ser Pro
145                 150                 155                 160

Arg Pro Pro Arg Leu Trp Cys Arg Gln Pro Arg His Val Arg Val Pro
                165                 170                 175

Gly Gln Cys Cys Glu Gln Trp Val Cys Asp Asp Ala Arg Arg Pro
            180                 185                 190

Arg Gln Thr Ala Leu Leu Asp Thr Arg Ala Phe Ala Ala Ser Gly Ala
        195                 200                 205

Val Glu Gln Arg Tyr Glu Asn Cys Ile Ala Tyr Thr Ser Pro Trp Ser
    210                 215                 220

```
Pro Cys Ser Thr Thr Cys Gly Leu Gly Ile Ser Thr Arg Ile Ser Asn
225                 230                 235                 240

Val Asn Ala Arg Cys Trp Pro Glu Gln Glu Ser Arg Leu Cys Asn Leu
            245                 250                 255

Arg Pro Cys Asp Val Asp Ile Gln Leu His Ile Lys Ala Gly Lys Lys
        260                 265                 270

Cys Leu Ala Val Tyr Gln Pro Glu Glu Ala Thr Asn Phe Thr Leu Ala
    275                 280                 285

Gly Cys Val Ser Thr Arg Thr Tyr Arg Pro Lys Tyr Cys Gly Val Cys
290                 295                 300

Thr Asp Asn Arg Cys Cys Ile Pro Tyr Lys Ser Lys Thr Ile Ser Val
305                 310                 315                 320

Asp Phe Gln Cys Pro Glu Gly Pro Gly Phe Ser Arg Gln Val Leu Trp
            325                 330                 335

Ile Asn Ala Cys Phe Cys Asn Leu Ser Cys Arg Asn Pro Asn Asp Ile
        340                 345                 350

Phe Ala Asp Leu Glu Ser Tyr Pro Asp Phe Glu Glu Ile Ala Asn
    355                 360                 365
```

<210> SEQ ID NO 4
<211> LENGTH: 5022
<212> TYPE: DNA
<213> ORGANISM: Mus musculus
<220> FEATURE:
<221> NAME/KEY: source
<222> LOCATION: 1..5022
<223> OTHER INFORMATION: /mol_type="unassigned DNA"
      /organism="Mus musculus"

<400> SEQUENCE: 4

| | | | | | |
|---|---|---|---|---|---|
| tgcagggcta | gtctgttggc | ctgacgtcag | atgtcgcttt | gacaaacgcc | cccgggggct | 60 |
| gaggaaggct | ctccgctgct | ctgatgggcc | agcccagtcc | tggcccagct | ccctggagag | 120 |
| gcatccgcat | cctctgggct | gagccgtagc | tcctgtgacg | ctgacttcca | ggcatgaggt | 180 |
| ggctcctgcc | ctggacgctg | gcagccgtgg | cagtcctgag | ggtgggcaac | atcctggcca | 240 |
| cggccctctc | tccaaccccc | acaacaatga | ccttcacccc | agcaccacta | gaggaaacga | 300 |
| ctacacgccc | cgaattctgc | aagtggccat | gtgagtgccc | acaatcccca | cctcgctgcc | 360 |
| cactgggcgt | cagcctaatc | acagatggct | gtgaatgctg | taagatatgt | gcccagcagc | 420 |
| ttggggacaa | ctgcacagag | gctgccatct | gtgacccaca | ccggggcctc | tactgcgatt | 480 |
| acagtgggga | tcgcccgagg | tacgcaatag | gagtgtgtgc | acaggtggtc | ggtgtgggct | 540 |
| gtgtcctgga | tggcgtacgc | tacaccaatg | gcgagtcctt | ccaacccaac | tgcaggtaca | 600 |
| actgtacctg | cattgatggc | acggtgggct | gcacaccgct | gtgcctaagc | ccaggcccc | 660 |
| cacgcctctg | gtgccgccag | ccccggcacg | tgagagtccc | tggccagtgc | tgtgagcagt | 720 |
| gggtgtgtga | tgatgacgca | aggagaccac | gccagactgc | actgttggac | accagagcct | 780 |
| ttgcagcgtc | aggcgccgtg | gagcaacggt | atgagaactg | catagcctac | actagtccct | 840 |
| ggagcccctg | ctctaccacc | tgtggcctag | gtatctccac | tcggatctct | aacgtcaatg | 900 |
| cccggtgctg | gccagagcag | gaaagtcgcc | tctgcaacct | gcggccatgt | gatgtggaca | 960 |
| tccaactaca | catcaaggca | gggaagaaat | gcctggctgt | gtaccagcca | gaggaggcca | 1020 |
| cgaacttcac | tctcgcaggc | tgtgtcagca | cacgcaccta | cgacccaag | tactgcggag | 1080 |
| tctgtactga | caataggtgt | tgcatcccct | acaagtccaa | gaccatcagt | gtggatttcc | 1140 |

```
agtgtccaga ggggccaggt ttctcccggc aggtcctatg gattaatgct tgcttctgca    1200
acctgagctg caggaatcct aacgatatct ttgctgactt ggaatcttac cctgacttcg    1260
aagagattgc caattaggtg ggtgtgtggc tcagggtaaa gttccatgct gcaaagcagc    1320
cagccctttg tggtccagga cttcacaatt gagccttatt tcatctactt cctactcgat    1380
tctgaattcc cagtttctgt tcctgttttg acaatcgtaa tggcccagga gagtgctgct    1440
caggctcaga caatgggttc ctccttgggg acattctaca tcattccaag gaaaacacat    1500
ctctgactgt tcacaatgga agcaaagcct ggcccagcta gtctggctcc agcctgggca    1560
agttgtcaga agttgtgatg ggattgtcca aggaaaagca tcagctgaag aaccagtatc    1620
atgaagtcct tcctcagatg ccaagcctag ggatgctggg atcctttcag acagatggat    1680
gggattgggg acacaggaat aagctattat tttacccttg ccaaatgata ctatcctggg    1740
tatttctgcc taaacatac caaaagtgtt cttgttccac tgatctgtat atcacaagtc    1800
accaaacatt ttccaggtga ggaccatagt tgtgtcattc tgttttgcta ttgaaaatca    1860
ttttaaaaag aaggaaaaaa aaaaagaaa agaaagaaa gtcatttcat taacttgggc    1920
actttctcct ctcaccccat attctataaa gggctaaact tggggttctt ttgatcagga    1980
atgtaatttg agaagtctta cttttgcagg agatggtag ccctcaattc atcccgtagg    2040
gatgggacaa ggccagccaa tcttttcaagc catagctggg caggtcactg aatctgctgc    2100
tggccaagtt cttaggacaa ttagccaaaa tctgggcctc tctctcccta gggttcatgg    2160
gagttggtag ggaccgtaga gtgacttgtc tgttgtctca aaaagtaaga tggaaagatg    2220
ttctcatggc ccttagaaga ctcttttgaa gtctacgcca gacctaacag aatatgtgca    2280
tcaaacaaac aagtggatca ccctcccatg gcctgggtga cctctagcag tcacccagtg    2340
actgtggtaa ggccacagta gtccctggac ccaggacaaa tctttttttgt ttcagtgacc    2400 tactttacag cctcagtgtc tatgaagaaa gttaactcag ttttctcatc tgaagacaga    2460
agtcgaccag ccattcagaa atggggatct atttagtagt ggtaaacgtt aaagagtttg    2520
taagctaaag aaatattttt tttcctaagt gataatgagg ttgttaccta ttttagaggt    2580
agaattttct gtcatcatcc ttttattgtg ttctacatac tacccattgt tctcaatatt    2640
tgccacacat ttactcattg aaacttgctg ataacacaga ggacttccct taatgatttc    2700
tgttcttgac actgtgaaat atcaattcaa agaggctaat aagttcaatc aaagtcacct    2760
atctgaagac tcatagccag agaagattgc cttcatattt cccctttgct tctggacctt    2820
gtaaacatgt cagggcagga aagcatacag aagtcagcag cttgccctct tagtattggc    2880
tctctagccc ctttcacgta agaggagagt gtgtctaggt actaaggatc caacctaaac    2940
tggacagaaa agggcatgtg cattatcccc tgtggctcct cctgccctgg aatcagaact    3000
agcttacagc atgcttttat atgatgattc agtttgcccc acaccataca tatgggcata    3060
tgggagaact atacacacac tcataaatgg atttgtaagt aggaaagggg acttgagatt    3120
tcccctcctt cctgcaactt cccaaaggcc tggccttatg caaggcaaac agtggtgctt    3180
aagatgtatt ttgggaagaa aatactatat atatatattc ctattttcc ttagaagcct    3240 tttcttccag gatctcatct taacagtaag aaatcctctc ttaagagagg cctagtatt    3300 tgagtaaaca tatgttcata tgtgtacaag tacttgtatg taaatataag ttaccactgt    3360
gggttattaa ttaggtaaat tttatgtggt atcatatttg attttcttct attggaaaaa    3420
tctgccttaa cagctaactc tgtaagaact tccataggag cctaagcta gggtcttccc    3480 aggtatccat cctctctttgg gaaactgagc tgagcatctt caaccaaagg agttagggtg    3540
```

```
atcattggga ataggagaaa gggatggcca gggtagctcc atcgttattt agaaacagac    3600
ctggcataca gaacgaccag aggaaccaac cttctttgaa ccaagggaaa aagacttgga    3660
tgtaatatat agaagctttt tctaatagtc agaaacagac tttaattgta tggcctggtt    3720
caaggaaagt taagaatgtc cattatcgtt aaaaacaaaa gtccattatt gatagcttat    3780
ttggtgctaa gccctacggt gcattttgtc cggctatcac ttagcagagc catgctcagt    3840
acacagtctt tctctattca ataaatgaaa acgctgaagc tcaaaggcac tgaggagctg    3900
aggctcagaa gcatgtttag tccactctat caggggggga agagatcttg acggaaccta    3960
aatgactact attggaaact catatttgaa agctttcaga agtcccaccc ccaccccatc    4020
cccagatgct tagaaactaa agaagcaatg aggatgagct agccttcagt gaagaggttc    4080
actactgcac caagagtgaa tgtcttaggt gtacttagtc attggacagg agacctgag     4140
tgagtttgtg aacctgcagc ttactaaacc ttacaatgag catttggaga gccaagactg    4200
cttctcggcg ctttactgac atggcttgct taatcttctc agtgagccca agagtcaggg    4260
cgttaccact gcccatttta gggctgagaa agcaaaatct ccaggagtta agtgatttgc    4320
tcaagttttt aaccaaccga ggcactgcag ataaactccg aagcccagtg tcatgtaaca    4380
tgcccatgcc atctctccgg acacgcagcc cattttcctg ttcctaaacc aaaggctcag    4440
agtcaccaga accaactcac aggacagtgc agaaattcta atgtcgaggg tgattagaga    4500
ctgatcaaag aaagtaattt caatgatat gattgtttgt aagcacccta gttaattctg     4560
gactacatat gcatagagat tgtgaagaac attacagcct gtgactataa cgttgacttc    4620
tgtcatttct tttaaagac ttgttttttt tttttactc aaaggaccca cagtgacagc      4680
cctgaatggt tgagaagcat tgattagctg tgagtcctgc atatgtatgt atgtgtgtgt    4740
gtgtgtgtgt atttgtatgt acttatctat tttcaaactg tgattgtgta tttaaatatt    4800
cctcctgcca ttttgtaagt gattacgcat aaagaaacac cttttgaatgt cctaataaag   4860
gagagctagc ccttgggcgg cctgtcacat tttgccactt tcctcatttt tctcatgatc    4920
tgtgtagcag ggaatgtgtt tgttcaacca tgatgagttt tcattgttca aattctttgt    4980
ttacagcttt tctccttaaa gcaataaatc atcagcaaca gt                       5022
```

<210> SEQ ID NO 5
<211> LENGTH: 163
<212> TYPE: PRT
<213> ORGANISM: Homo sapiens
<400> SEQUENCE: 5

```
Met Arg Trp Phe Leu Pro Trp Thr Leu Ala Ala Val Thr Ala Ala
1               5                   10                  15

Ala Ser Thr Val Leu Ala Thr Ala Leu Ser Pro Ala Pro Thr Thr Met
                20                  25                  30

Asp Phe Thr Pro Ala Pro Leu Glu Asp Thr Ser Ser Arg Pro Gln Phe
            35                  40                  45

Cys Lys Trp Pro Cys Glu Cys Pro Ser Pro Arg Cys Pro Leu
        50                  55                  60

Gly Val Ser Leu Ile Thr Asp Gly Cys Glu Cys Lys Met Cys Ala
65                  70                  75                  80

Gln Gln Leu Gly Asp Asn Cys Thr Glu Ala Val Ile Cys Asp Pro His
                85                  90                  95

Arg Gly Leu Tyr Cys Asp Tyr Ser Gly Asp Arg Pro Arg Tyr Ala Ile
            100                 105                 110
```

Gly Val Cys Ala Arg Arg Glu Glu Val Ser Gly Cys Val Pro Ala Arg
            115                 120                 125

Gly Ile His Glu Leu His Thr Cys Gly Leu His Gln His Thr Leu Leu
        130                 135                 140

Ser Thr Gln Val Leu Trp Ser Leu His Gly Gln Gln Val Leu His Pro
145                 150                 155                 160

Leu Gln Val

<210> SEQ ID NO 6
<211> LENGTH: 716
<212> TYPE: DNA
<213> ORGANISM: Homo sapiens
<220> FEATURE:
<221> NAME/KEY: source
<222> LOCATION: 1..716
<223> OTHER INFORMATION: /mol_type="unassigned DNA"
      /organism="Homo sapiens"

<400> SEQUENCE: 6
ccgagaggtg gtcggatcct ctgggctgct cggtcgatgc ctgtgccact gacgtccagg      60
catgaggtgg ttcctgccct ggacgctggc agcagtgaca gcagcagccg ccagcaccgt     120
cctggccacg gccctctctc agcccctac gaccatggac tttaccccag ctccactgga      180
ggacacctcc tcacgccccc aattctgcaa gtggccatgt gagtgcccgc catccccacc     240
ccgctgcccg ctgggggtca gcctcatcac agatggctgt gagtgctgta agatgtgcgc     300
tcagcagctt ggggacaact gcacggaggc tgtcatctgt gacccccacc ggggcctcta     360
ctgtgactac agcggggacc gcccgaggta cgcaatagga gtgtgtgcac gcagggaaga     420
agtgtctggc tgtgtaccag ccagaggcat ccatgaactt cacacttgcg ggctgcatca     480
gcacacgctc ctatcaaccc aagtactgtg gagtttgcat ggacaacagg tgctgcatcc     540
cctacaagtc taagactatc gacgtgtcct ccagtgtcc tgatgggctt ggcttctccc      600
gccaggtcct atggattaat gcctgcttct gtaacctgag ctgtaggaat cccaatgaca     660
tctttgctga cttggaatcc taccctgact ctcagaaaat tgccaactag gcaggc        716

<210> SEQ ID NO 7
<211> LENGTH: 195
<212> TYPE: PRT
<213> ORGANISM: Homo sapiens

<400> SEQUENCE: 7

Met Pro Val Pro Leu Thr Ser Arg His Glu Val Pro Ala Leu Asp
1               5                   10                  15

Ala Gly Ser Ser Asp Ser Ser Arg Gln His Arg Pro Gly His Asp
            20                  25                  30

Ala Val Gly Glu Val Glu Ala Trp His Arg Asn Cys Ile Ala Tyr Thr
        35                  40                  45

Ser Pro Trp Ser Pro Cys Ser Thr Ser Cys Gly Leu Gly Val Ser Thr
    50                  55                  60

Arg Ile Ser Asn Val Asn Ala Gln Cys Trp Pro Glu Gln Glu Ser Arg
65                  70                  75                  80

Leu Cys Asn Leu Arg Pro Cys Asp Val Asp Ile His Thr Leu Ile Lys
                85                  90                  95

Ala Gly Lys Lys Cys Leu Ala Val Tyr Gln Pro Glu Ala Ser Met Asn
            100                 105                 110

Phe Thr Leu Ala Gly Cys Ile Ser Thr Arg Ser Tyr Gln Pro Lys Tyr

```
            115                 120                 125
Cys Gly Val Cys Met Asp Asn Arg Cys Cys Ile Pro Tyr Lys Ser Lys
        130                 135                 140

Thr Ile Asp Val Ser Phe Gln Cys Pro Asp Gly Leu Gly Phe Ser Arg
145                 150                 155                 160

Gln Val Leu Trp Ile Asn Ala Cys Phe Cys Asn Leu Ser Cys Arg Asn
                165                 170                 175

Pro Asn Asp Ile Phe Ala Asp Leu Glu Ser Tyr Pro Asp Phe Ser Glu
                180                 185                 190

Ile Ala Asn
        195

<210> SEQ ID NO 8
<211> LENGTH: 630
<212> TYPE: DNA
<213> ORGANISM: Homo sapiens
<220> FEATURE:
<221> NAME/KEY: source
<222> LOCATION: 1..630
<223> OTHER INFORMATION: /mol_type="unassigned DNA"
      /organism="Homo sapiens"

<400> SEQUENCE: 8
ccgagaggtg gtcggatcct ctgggctgct cggtcgatgc ctgtgccact gacgtccagg      60
catgaggtgg ttcctgccct ggacgctggc agcagtgaca gcagcagccg ccagcaccgt     120
cctggccacg atgctgtggg tgaggtggag gcatggcaca ggaactgcat agcctacaca     180
agcccctgga gccttgctc caccagctgc ggcctggggg tctccactcg gatctccaat     240
gttaacgccc agtgctggcc tgagcaagag agccgcctct gcaacttgcg ccatgcgat      300 gtggacatcc atacactcat taaggcaggg aagaagtgtc tggctgtgta ccagccagag     360
gcatccatga acttcacact tgcgggctgc atcagcacac gctcctatca acccaagtac     420
tgtggagttt gcatggacaa taggtgctgc atcccctaca gtctaagac tatcgacgtg      480 tccttccagt gtcctgatgg gcttggcttc tcccgccagg tcctatggat taatgcctgc     540
ttctgtaacc tgagctgtag gaatcccaat gacatctttg ctgacttgga atcctaccct     600
gacttctcag aaattgccaa ctaggcaggc                                      630

<210> SEQ ID NO 9
<211> LENGTH: 122
<212> TYPE: PRT
<213> ORGANISM: Homo sapiens

<400> SEQUENCE: 9

Met Arg Trp Phe Leu Pro Trp Thr Leu Ala Ala Val Thr Ala Ala Ala
1               5                   10                  15

Ala Ser Thr Val Leu Ala Thr Ala Gly Lys Lys Cys Leu Ala Val Tyr
                20                  25                  30

Gln Pro Glu Ala Ser Met Asn Phe Thr Leu Ala Gly Cys Ile Ser Thr
            35                  40                  45

Arg Ser Tyr Gln Pro Lys Tyr Cys Gly Val Cys Met Asp Asn Arg Cys
        50                  55                  60

Cys Ile Pro Tyr Lys Ser Lys Thr Ile Asp Val Ser Phe Gln Cys Pro
65                  70                  75                  80

Asp Gly Leu Gly Phe Ser Arg Gln Val Leu Trp Ile Asn Ala Cys Phe
                85                  90                  95

Cys Asn Leu Ser Cys Arg Asn Pro Asn Asp Ile Phe Ala Asp Leu Glu
```

```
            100                 105                 110
Ser Tyr Pro Asp Phe Ser Glu Ile Ala Asn
        115                 120
```

<210> SEQ ID NO 10
<211> LENGTH: 573
<212> TYPE: DNA
<213> ORGANISM: Homo sapiens
<220> FEATURE:
<221> NAME/KEY: source
<222> LOCATION: 1..573
<223> OTHER INFORMATION: /mol_type="unassigned DNA"
      /organism="Homo sapiens"

<400> SEQUENCE: 10

```
gcgtccgctg ggcccagctc ccccgagagg tggtcggatc ctctgggctg ctcggtcgat      60
gcctgtgcca ctgacgtcca ggcatgaggt ggttcctgcc ctggacgctg gcagcagtga     120
cagcagcagc cgccagcacc gtcctggcca cggcagggaa gaagtgtctg gctgtgtacc     180
agccagaggc atccatgaac ttcacacttg cgggctgcat cagcacacgc tcctatcaac     240
ccaagtactg tggagtttgc atggacaaca ggtgctgcat ccctacaag tctaagacta      300 tcgacgtgtc cttccagtgt cctgatgggc ttggcttctc ccgccaggtc ctatggatta    360
atgcctgctt ctgtaacctg agctgtagga atcccaatga catctttgct gacttggaat    420
cctaccctga cttctcagaa attgccaact aggcaggcac aaatcttggg tcttggggac    480
taacccaatg cctgtgaagc agtcagccct tatggccaat aactttcac caatgagcct      540 tagttaccct gaaaaaaaaa aaaaaaaaa aaa                                    573
```

METHODS FOR TREATING SARCOPENIA AND MUSCLE INJURY

CROSS REFERENCE TO RELATED APPLICATIONS

The present application is a National Stage of International Application No. PCT/EP2017/063238, filed on Jun. 1, 2017, which claims priority to European Patent Application No. 16172719.3, filed on Jun. 2, 2016, the entire contents of which are being incorporated herein by reference.

FIELD OF THE INVENTION

The present invention relates to the use of Wnt-inducible signalling protein 1 (WISP1) for improving muscle regeneration to facilitate maintenance or increase in muscle function and/or muscle mass, for example in ageing subjects and/or subjects suffering from muscle injury. In particular, the invention relates to the use of WISP1 for treating sarcopenia or physical frailty; and/or treating muscle injury.

BACKGROUND TO THE INVENTION

Age-related loss of muscle function and mass occurs inevitably in all individuals, however its progression depends on a range of genetic and environmental factors, such as physical activity and nutritional intake.

In some subjects, the effect of ageing on muscle may progress to a state of morbidity, specific conditions of which include sarcopenia and frailty. Sarcopenia is defined as occurring at the point at which the age-related loss of muscle function and mass becomes debilitating and impacts on quality of life (Sayer, A. A. et al. (2013) Age Ageing 42: 145-150). In contrast, frailty is a classification of age-related muscle dysfunction which relies on muscle strength and functionality, but not muscle mass (Morley, J. E. et al. (2013) J. Am. Med. Dir. Assoc. 14: 392-397).

Sarcopenia and frailty are multi-factorial syndromes which associate with pathophysiological changes, such as impaired neuro-muscular transition, altered excitation/contraction coupling, impaired regenerative capacity linked to stem cell exhaustion, defects of mitochondrial and energy metabolism in myofibers, and marbling of skeletal muscle with fat and fibrosis (Ali, S. et al. (2014) Gerontology 60: 294-305). The aetiology of these syndromes is therefore complex and poorly understood, but low physical activity, hormonal decline in anabolic hormones (e.g. androgens and IGF-1), and malnutrition and/or nutritional deficiencies play an important role (Mithal, A. et al. (2013) Osteoporos. Int. 24: 1555-1566).

Sarcopenia is becoming a major health concern in developed countries, where lessened physical activity with age and increased longevity are particularly prevalent. In severe cases, sarcopenia may result in a person losing their ability to live independently. In addition, sarcopenia is a predictor of wider-ranging disability in population-based studies, and has been linked to poor balance, gait speed, prevalence of falls and fractures.

Reduced physical activity is thought to increase the likelihood of sarcopenia and therefore increased exercise will likely be beneficial in combatting the condition. Indeed, resistance exercise is associated with increased synthesis of proteins in skeletal muscle. However, exercise as a treatment often suffers from poor patient compliance.

There are currently no pharmacological agents approved for the treatment of sarcopenia. A number of growth hormones have been studied in this context, however these have shown little effect. In addition, anabolic steroids may increase muscle mass and strength, but are associated with a number of side effects, such as increased risk of prostate cancer.

Similarly, a negative impact on muscle function and mass may also result from muscle injury, for example following trauma or medical intervention (e.g. surgery). The impact of such events may be more severe in ageing subjects who may experience more difficult and/or longer rehabilitation following the injury.

Although physiotherapy may aid rehabilitation following muscle injury, this may also suffer from poor patient compliance. In addition, further methods may be required to complement physiotherapy approaches to increase their ease and effectiveness.

Accordingly there remains a significant need for methods of improving muscle regeneration to facilitate maintenance or increase in muscle function and/or muscle mass, for example in ageing subjects. In particular, there is a need for methods of treating sarcopenia and frailty; and/or methods of treating muscle injury.

SUMMARY OF THE INVENTION

The present inventors have identified Wnt-inducible signalling protein 1 (WISP1) as a protein that is strongly expressed during muscle regeneration. In addition, the inventors have discovered that WISP1 levels decrease in a subject with age.

The inventors demonstrated that WISP1 is expressed by several muscle resident cell types upon muscle injury, but mostly by the fibro/adipogenic progenitor (FAP) cells whose expression of WISP-1 also strongly decreases with age. Furthermore, the inventors' results also suggest a role for WISP1 in deterioration of whole muscle function with age, because they show that WISP1 levels are strongly down-regulated in aged non-injured muscles and sarcopenic rat serum.

By applying WISP1, the inventors were able to improve defective adhesion and proliferation properties of old satellite cells (muscle stem cells) ex vivo, as well as enhancing young satellite cell function. In vivo, WISP1 treatment of old subject during regeneration translated into an increased activation of progenitor markers and faster recovery of regenerated fibers a few days after injury. Thus, while not wishing to be bound by theory, WISP1 appears to increase muscle regeneration by promoting muscle stem cell function.

In summary, the inventors have unexpectedly found that increasing levels of WISP1 is clinically applicable to the treatment of reduced muscle function and mass, in particular in ageing subjects.

Accordingly, in one aspect the invention provides Wnt-inducible signalling protein 1 (WISP1) or a fragment or variant thereof for use in maintaining or increasing muscle function and/or mass in a subject, and/or substantially preventing or reducing muscle wasting in a subject. In one aspect, said use is non-therapeutic.

In another aspect, the invention provides a method of maintaining or increasing muscle function and/or mass in a subject, and/or substantially preventing or reducing muscle wasting in a subject comprising administering Wnt-inducible signalling protein 1 (WISP1) or a fragment or variant thereof to a subject in need thereof.

In one embodiment, the WISP1 or fragment or variant thereof maintains or increases muscle mass.

In another embodiment, the WISP1 or fragment or variant thereof substantially prevents or reduces a reduction in muscle mass. The prevention or reduction in muscle mass may be in comparison to the reduction in muscle mass that would be expected in the absence of the WISP1 or fragment or variant thereof of the invention.

In another aspect, the invention provides Wnt-inducible signalling protein 1 (WISP1) or a fragment or variant thereof for use in treating or preventing sarcopenia, frailty and/or muscle injury in a subject.

In another aspect, the invention provides a method of treating or preventing sarcopenia, frailty and/or muscle injury comprising administering Wnt-inducible signalling protein 1 (WISP1) or a fragment or variant thereof to a subject in need thereof.

In one embodiment, the muscle is skeletal muscle.

In one embodiment, the subject is an ageing subject.

The ageing subject may be, for example, a human subject over the age of 30, 35, 40, 45, 50, 55, 60, 65, 70, 75, 80, 85, 90, 95 or 100 years old.

In one embodiment, the subject has incurred muscle injury through a surgical intervention and/or trauma.

In another embodiment, the subject is to undergo a planned surgical intervention.

In one embodiment, the WISP1 fragment or variant:
(a) lacks the VWC, TSP1 and CT domains;
(b) lacks the IGFB and VWC domains; or
(c) consists of the CT domain.

In one embodiment, the WISP1 fragment or variant lacks the VWC, TSP1 and CT domains. In another embodiment, the WISP1 fragment or variant lacks the IGFB and VWC domains. In another embodiment, the WISP1 fragment or variant consists of the CT domain.

In one embodiment, the WISP1 or fragment or variant thereof comprises an amino acid sequence that has at least 60% identity to SEQ ID NO: 1, 3, 5, 7 or 9, preferably SEQ ID NO: 1, 5, 7 or 9, more preferably SEQ ID NO: 1.

Preferably, the WISP1 or fragment or variant thereof provides for maintaining or increasing muscle function and/or mass in a subject and/or substantially preventing or reducing muscle wasting in a subject. Preferably, the WISP1 or fragment or variant thereof substantially retains the natural function of the protein represented by SEQ ID NO: 1.

In another embodiment, the WISP1 or fragment or variant thereof comprises an amino acid sequence that has at least 60%, 70%, 80%, 90%, 95%, 96%, 97%, 98%, 99% or 100% identity to SEQ ID NO: 1, 3, 5, 7 or 9, preferably SEQ ID NO: 1, 5, 7 or 9, more preferably SEQ ID NO: 1. Preferably, the WISP1 or fragment or variant thereof provides for maintaining or increasing muscle function and/or mass in a subject and/or substantially preventing or reducing muscle wasting in a subject. Preferably, the WISP1 or fragment or variant thereof substantially retains the natural function of the protein represented by SEQ ID NO: 1.

Preferably, the WISP1 or fragment or variant thereof provides a similar or increased effect of:
(a) maintaining or increasing muscle function and/or mass in a subject;
(b) preventing or reducing muscle wasting in a subject; and/or
(c) treating or preventing sarcopenia, frailty and/or muscle injury in a subject, compared to the protein of SEQ ID NO: 1.

The WISP1 or fragment or variant thereof disclosed herein may be, for example, administered systemically or locally. In one embodiment, the WISP1 or fragment or variant thereof is administered parenterally, for example via sub-cutaneous, intravenous or intramuscular injection.

In one embodiment, the WISP1 or fragment or variant thereof is administered using a vector (e.g. a viral vector, such as a retroviral, lentiviral, adenoviral or adeno-associated viral vector) comprising a polynucleotide sequence encoding the WISP1 or fragment or variant thereof.

In another aspect, the invention provides the use of the Wnt-inducible signalling protein 1 (WISP1) or fragment or variant thereof disclosed herein for the manufacture of a medicament for:
(a) maintaining or increasing muscle function and/or mass in a subject;
(b) substantially preventing or reducing muscle wasting in a subject; and/or
(c) treating or preventing sarcopenia, frailty and/or muscle injury in a subject.

In another aspect, the invention provides the use of the Wnt-inducible signalling protein 1 (WISP1) or fragment or variant thereof disclosed herein for:
(a) maintaining or increasing muscle function and/or mass in a subject;
(b) substantially preventing or reducing muscle wasting in a subject; and/or
(c) treating or preventing sarcopenia, frailty and/or muscle injury in a subject.

In one embodiment, the medicament or WISP1 disclosed herein maintains or increases muscle mass.

In another embodiment, the medicament or WISP1 disclosed herein substantially prevents or reduces a reduction in muscle mass.

In another aspect, the invention provides the use of the Wnt-inducible signalling protein 1 (WISP1) or a fragment or variant thereof disclosed herein for increasing muscle stem and/or progenitor cell proliferation (e.g. satellite (SAT) and/or fibro/adipogenic progenitor (FAP) cell proliferation). The proliferation of the muscle stem and/or progenitor cells may be, for example, at least 1%, 2%, 3%, 4%, 5%, 10%, 20%, 30%, 40%, 50%, 75% or 100% greater in the presence of the WISP1 or fragment or variant thereof disclosed herein, than in its absence. Such cell proliferation may be measured using any suitable means known in the art.

The use may be, for example, an in vitro or ex vivo use, preferably an in vitro use.

The WISP1 or fragment or variant thereof may be used in an ex vivo cell therapy protocol. In one aspect, the invention provides a population of cells for use in:
(a) maintaining or increasing muscle function and/or mass in a subject;
(b) substantially preventing or reducing muscle wasting in a subject; and/or
(c) treating or preventing sarcopenia, frailty and/or muscle injury in a subject,
wherein the population of cells is cultured ex vivo in the presence of the Wnt-inducible signalling protein 1 (WISP1) or fragment or variant thereof disclosed herein. The population of cells may be, for example, a population of muscle cells, in particular muscle stem and/or progenitor cells (e.g. satellite (SAT) and/or fibro/adipogenic progenitor (FAP) cells). The population of cells may be administered to a subject in the presence of WISP1.

In another aspect, the invention provides a method of screening for an agent capable of increasing Wnt-inducible signalling protein 1 (WISP1) levels in a subject comprising the steps:

(a) contacting a population of cells with a candidate agent;
(b) determining the level of WISP1 in the population of cells; and
(c) comparing the level of WISP1 determined in step (b) with a WISP1 level in a control population of cells which has not been contacted with the candidate agent.

In another aspect, the invention provides a method of screening for an agent capable of maintaining or increasing muscle function and/or mass in a subject; substantially preventing or reducing muscle wasting in a subject; and/or treating or preventing sarcopenia, frailty and/or muscle injury in a subject, comprising the steps:
(a) contacting a population of cells with a candidate agent;
(b) determining the level of WISP1 in the population of cells; and
(c) comparing the level of WISP1 determined in step (b) with a WISP1 level in a control population of cells which has not been contacted with the candidate agent.

The candidate agent may be, for example, a pharmaceutical agent or nutritional supplement. Preferably, the candidate agent is a nutritional supplement.

In one embodiment, the candidate agent is comprised in a library of candidate agents.

In another aspect, the invention provides an agent for increasing Wnt-inducible signalling protein 1 (WISP1) levels in a subject, preferably wherein the agent has been identified by a method of screening disclosed herein.

Preferably, the agent is a nutritional supplement.

In another aspect, the invention provides the agent of the invention for use in:
(a) maintaining or increasing muscle function and/or mass in a subject;
(b) substantially preventing or reducing muscle wasting in a subject; and/or
(c) treating or preventing sarcopenia, frailty and/or muscle injury in a subject.

In another aspect, the invention provides a method of diagnosing sarcopenia or frailty comprising the steps:
(a) providing a biological sample isolated from a subject;
(b) determining the level of Wnt-inducible signalling protein 1 (WISP1) in the biological sample; and
(c) comparing the level of WISP1 determined in step (b) with a WISP1 level determined from one or more control samples or reference levels.

In another aspect, the invention provides a method of maintaining or increasing muscle function and/or mass in a subject, and/or substantially preventing or reducing muscle wasting in a subject comprising administering the Wnt-inducible signalling protein 1 (WISP1) or a fragment or variant thereof disclosed herein to a subject who has been diagnosed as having sarcopenia or being at risk of developing sarcopenia, or diagnosed as being frail or at being at risk of becoming frail using a method disclosed herein.

In another aspect, the invention provides a method of treating or preventing sarcopenia, frailty and/or muscle injury comprising administering the Wnt-inducible signalling protein 1 (WISP1) or a fragment or variant thereof disclosed herein to a subject who has been diagnosed as having sarcopenia or being at risk of developing sarcopenia, or diagnosed as being frail or at being at risk of becoming frail using a method disclosed herein.

In another aspect, the invention provides a diet product comprising WISP1 or a fragment or variant thereof for use in maintaining or increasing muscle function and/or mass in a subject, and/or substantially preventing or reducing muscle wasting in a subject.

In another aspect, the invention provides a diet product described herein for use in treating or preventing sarcopenia, frailty and/or muscle injury in a subject.

Preferably, the diet product of the invention is for use in a subject who has been diagnosed as having sarcopenia or being at risk of developing sarcopenia, or diagnosed as being frail or at being at risk of becoming frail using a method disclosed herein.

In another aspect, the invention provides for a modulator of endogenous WISP-1 which is preferably administered alone or together with the WISP1 or fragment or variant thereof disclosed herein, for example, administered systemically or locally.

In one embodiment, the modulator of endogenous WISP-1 is administered together with the WISP1 or fragment or variant parenterally, for example via sub-cutaneous, intravenous or intramuscular injection.

In another aspect, the Wnt-inducible signalling protein 1 (WISP1) or fragment or variant thereof; agent; or diet product of the invention may be used in combination with an exercise regime.

Figure 1A:
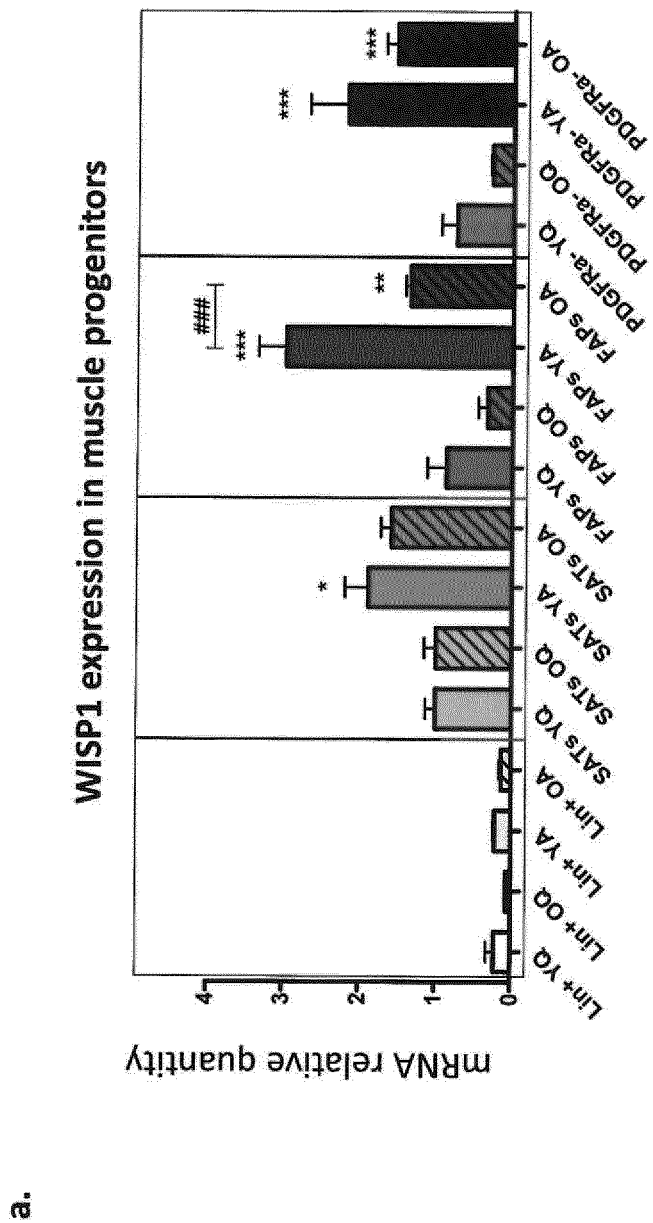
FIG. 1

WISP1 is differentially expressed with age (a) WISP1 expression in freshly isolated cells, assessed by qPCR. Satellite cells (SATs; CD31−/CD11b−/CD45−/Sca1−/CD34+/Integrin α7+); Fibro/adipogenic Progenitors (FAPs; CD31−/CD11b−/CD45−/Sca1+/CD34+/PDGFRα+); Lineage cells (Lin+; CD31+/CD11b+/CD45+); and PDGFRα− cells (CD31−/CD11b−/CD45−/Sca1+/CD34+/PDGFRα−) were isolated from young (Y) and old (O) mice, either from uninjured muscles (quiescent cells; Q) or 3 days after muscle injury (activated cells; A). Data were normalised to YQ SATs; *: p-value v. young quiescent respective cell type<0.05; : p-value v. young quiescent respective cell type<0.01; *: p-value v. young quiescent respective cell type<0.001; ###: p-value old v. young activated respective cell type<0.001, n>4.

(b) Left graph—WISP1 expression in full regenerating muscles, assessed by qPCR. Young and old muscles were injured, and muscles were collected for biomolecular analysis at 3, 7 and 14 days post injury (dpi). Data were normalised to young non-injured muscles (control); *: p-value v. young control<0.05; : p-value v. young control<0.01; *: p-value v. young control<0.001; ###: p-value old v. young at respective time points<0.001, n=8. Right graph—highlights expression values in non-injured muscles, ##: p-value old v. young<0.01, n=8.

(c) WISP1 protein level in regenerating muscles, measured by SOMALOGICS. Young and old muscles were injured, and muscles were collected for biomolecular analysis at 3, 7 and 14 days post injury (dpi); *: p-value v. young control<0.05; : p-value v. young control<0.01; *: p-value v. young control<0.001; ##: p-value old v. young at respective time points<0.01, n=8.

(d) WISP1 protein level in rat serums, measured by SOMALOGICS. : p-value vs. 8 month-old rats<0.01, *: p-value vs. 8 month-old rats<0.001, n>9.

FIG. 2

WISP1 regulates muscle stem cell function (a) Adhesion of satellite cells ex vivo, upon mrWISP1 treatment. Young (top graph) and old (bottom graph) freshly isolated satellite cells were seeded on 0.2% collagen coated plates in medium containing either PBS, 1 ug/mL mrWISP1 or 8 ug/mL mrWISP1, fixed and counted 36 h after seeded to assess adhesion.

(b,c) Proliferation of satellite cells ex vivo, upon mrWISP1 treatment. Young (top graph) and old (bottom graph) freshly isolated satellite cells were seeded on 0.2% collagen coated plates in medium containing either PBS, 1 ug/mL mrWISP1 or 8 ug/mL mrWISP1; or allowed to proliferate during 3 days. Proliferating cells received a 10 uM EdU pulse for 3 hours, were fixed and assessed for proliferation based on the total number of cells (b) or percentage of EdU+ cells (c). Data are normalized to non-treated cells, *: p-value vs. PBS<0.05, : p-value vs. PBS<0.01, *: p-value vs. PBS<0.001, n>16 technical replicates.

(d) Proliferation of HSMM in vitro upon mrWISP1 treatment. HSMM were allowed to proliferate during 3 days and received a 10 uM EdU pulse for 3 hours, were fixed and stained for EdU. Data are normalized to non-treated cells, *: p-value vs. PBS<0.05, : p-value vs. PBS<0.01, *: p-value vs. PBS<0.001, n>16 technical replicates.

(e) Young satellite cells differentiation upon mrWISP1 treatment. SATs were allowed to proliferate in growth medium, and were induced to differentiate in differentiation medium containing WISP1 for 2 days. Data are normalized to non-treated cells, n.s: p-value vs. PBS>0.05, **: n>16 technical replicates, n=3 independent experiments with independent biological replicates.

FIG. 3

WISP1 in vivo treatment ameliorates muscle regeneration in old mice, at the biomolecular level qPCR of different myogenic markers (Pax7, MyoD, myogenin and Myh3), in full regenerating muscles. Old (O) muscles were injured, and muscles were collected for biomolecular analysis at 3, 7 and 14 days post injury (dpi). Mice were treated daily with PBS or 1 mg/kg/day of mrWISP1. Data were normalised to gene expression in contralateral non-injured tibialis anterior muscles (TA cl); *: p-value v. TA cl<0.05; : p-value v. TA cl<0.01; *: p-value v. TA cl<0.001; #: p-value WISP1 v. PBS treated mice<0.05; ##: p-value WISP1 v. PBS treated mice<0.01; ###: p-value WISP1 v. PBS treated mice<0.001, n>6.

FIG. 4

WISP1 in vivo treatment enhances the expression of markers correlated with FAPsqPCR of FAPs activity markers (PDGFRa, Fibronectin (FN) and WISP1) in full regenerating muscles. Old (O) muscles were injured, and muscles were collected for biomolecular analysis at 3, 7 and 14 days post injury (dpi). Mice were treated daily with PBS or 1 mg/kg/day of mrWISP1. Data were normalised to gene expression in contralateral non-injured tibialis anterior muscles (TA cl); *: p-value v. TA cl<0.05; : p-value v. TA cl<0.01; *: p-value v. TA cl<0.001; #: p-value WISP1 v. PBS treated mice<0.05; ##: p-value WISP1 v. PBS treated mice<0.01; ###: p-value WISP1 v. PBS treated mice<0.001, n>6.

FIG. 5

WISP1 in vivo treatment rescues muscle regeneration at the histological level

Muscle sections were stained with embryonic myosin heavy chain (eMHC), a marker of newly formed fibers, and the area covered by eMHC+ fibers was quantified. Young (Y) and old (O) muscles were injured, and muscles were collected for histological analysis at 7 and 14 days post injury (dpi). Mice were treated daily with PBS or 1 mg/kg/day of mrWISP1. #: p-value WISP1 v. PBS treated mice<0.05.

DETAILED DESCRIPTION OF THE INVENTION

Various preferred features and embodiments of the present invention will now be described by way of non-limiting examples.

The practice of the present invention will employ, unless otherwise indicated, conventional techniques of chemistry, biochemistry, molecular biology, microbiology and immunology, which are within the capabilities of a person of ordinary skill in the art. Such techniques are explained in the literature. See, for example, Sambrook, J., Fritsch, E. F. and Maniatis, T. (1989) Molecular Cloning: A Laboratory Manual, 2nd Edition, Cold Spring Harbor Laboratory Press; Ausubel, F. M. et al. (1995 and periodic supplements) Current Protocols in Molecular Biology, Ch. 9, 13 and 16, John Wiley & Sons; Roe, B., Crabtree, J. and Kahn, A. (1996) DNA Isolation and Sequencing: Essential Techniques, John Wiley & Sons; Polak, J. M. and McGee, J. O'D. (1990) In Situ Hybridization: Principles and Practice, Oxford University Press; Gait, M. J. (1984) Oligonucleotide Synthesis: A Practical Approach, IRL Press; and Lilley, D. M. and Dahlberg, J. E. (1992) Methods in Enzymology: DNA Structures Part A: Synthesis and Physical Analysis of DNA, Academic Press. Each of these general texts is herein incorporated by reference.

Wnt-Inducible Signalling Protein 1 (WISP1)

Wnt-inducible signalling protein 1 (WISP1) is a secreted extra-cellular matrix-associated protein, also known as connective tissue growth factor (CTGF).

WISP1 is the $4^{th}$ member of 6 CCN family matricellular proteins. The CCN proteins contain 4 conserved functional domains that are thought to act both independently and cooperatively to contribute to a range of cellular functions (Hall-Glenn, F. et al. (2011) Cell. Mol. Life Sci. 68: 3209-17). The four functional domains allow binding of the CCN proteins to many signalling molecules and extracellular matrix proteins, thus potentially inducing multiple cellular signalling pathways.

WISP1 has been shown to regulate various biological processes such as neuronal development, neurogenesis, stem cell, survival and angiogenesis (Maiese, K. (2014) Curr. Neurovasc. Res. 11: 378-89). An oncogenic role for WISP1 was demonstrated in breast cancer (Chiang, K. C. et al. (2015) Sci. Rep. 5: 8686; Klinke, D. J. (2014) PLoS Comput. Biol. 10; e1003409), and WISP1 function has been correlated with tumour cell growth and progression (Maiese, K. (2014) Curr. Neurovasc. Res. 11: 378-89; Nagai, Y. et al. (2011) Anticancer Res. 31: 991-7). However, direct links between WISP1 and carcinogenesis remain to be elucidated. WISP1 has also been suggested to play a tumour suppressor role in other contexts (Hashimoto, Y. et al. (1998) J. Exp. Med. 187: 289-96). WISP1 was shown to exert mitogenic effects in rat fibroblasts in vitro and in vivo (Xu, L. et al. (2000) Genes Dev. 14: 585-95), and it was further demonstrated that WISP1 secreted by fibroblasts could act through paracrine signalling (Tanaka, S. et al. (2001) Oncogene. 20: 5525-32). The CCN protein, has also been studied in tissue repair contexts. Indeed, WISP1 expression has been shown to be elevated after cardiac ischemia (Colston, J. T. et al. (2007) Am. J. Physiol. Heart Circ. Physiol. 293: H1839-46), damage of lung epithelium (Heise, R. L. et al. (2011) J. Biol. Chem. 286: 17435-44), bone fracture (French, D. M. et al. (2004) Am. J. Pathol. 165: 855-67; Macsai, C. E. et al. (2012) Bone 50: 1081-91) and upon oxidative stress of neuronal tissue (Wang, S. et al. (2012) Curr. Neurovasc. Res. 9: 91-101; Wang, S. et al. (2012) Curr. Neurovasc. Res. 9:

20-31). Recently, a novel role for WISP1 has been suggested in metabolism and adipose tissue biology. Indeed WISP1 was found to be secreted by adipocytes during differentiation and to be associated with markers of insulin resistance in adipose tissue (Murahovschi, V. et al. (2015) Diabetes 64: 856-66). Weight loss in mice and humans was associated with decreased WISP1 levels in fat depots and blood, and it was suggested that WISP1 might maintain an inflammatory state within the adipose tissue.

However, a role for WISP1 in skeletal muscle and muscle stem cells has not previously been demonstrated.

In one embodiment, the WISP1 or fragment or variant thereof is human WISP1 or a fragment or variant thereof.

An example amino acid sequence of WISP1 is:

```
                                (SEQ ID NO: 1; human WISP1)
MRWFLPWTLAAVTAAAASTVLATALSPAPTTMDFTPAPLEDTSSRPQFCK

WPCECPPSPPRCPLGVSLITDGCECCKMCAQQLGDNCTEAAICDPHRGLY

CDYSGDRPRYAIGVCAQVVGVGCVLDGVRYNNGQSFQPNCKYNCTCIDGA

VGCTPLCLRVRPPRLWCPHPRRVSIPGHCCEQWVCEDDAKRPRKTAPRDT

GAFDAVGEVEAWHRNCIAYTSPWSPCSTSCGLGVSTRISNVNAQCWPEQE

SRLCNLRPCDVDIHTLIKAGKKCLAVYQPEASMNFTLAGCISTRSYQPKY

CGVCMDNRCCIPYKSKTIDVSFQCPDGLGFSRQVLWINACFCNLSCRNPN

DIFADLESYPDFSEIAN
```

An example polynucleotide sequence encoding WISP1 is:

```
                                (SEQ ID NO: 2; human WISP1)
CCCACGCGTCCGCTGGGCCCAGCTCCCCCGAGAGGTGGTCGGATCCTCTG

GGCTGCTCGGTCGATGCCTGTGCCACTGACGTCCAGGCATGAGGTGGTTC

CTGCCCTGGACGCTGGCAGCAGTGACAGCAGCAGCCGCCAGCACCGTCCT

GGCCACGGCCCTCTCTCCAGCCCCTACGACCATGGACTTTACTCCAGCTC

CACTGGAGGACACCTCCTCACGCCCCCAATTCTGCAAGTGGCCATGTGAG

TGCCCGCCATCCCCACCCCGCTGCCCGCTGGGGGTCAGCCTCATCACAGA

TGGCTGTGAGTGCTGTAAGATGTGCGCTCAGCAGCTTGGGGACAACTGCA

CGGAGGCTGCCATCTGTGACCCCCACCGGGCCTCTACTGTGACTACAGC

GGGGACCGCCCGAGGTACGCAATAGGAGTGTGTGCACAGGTGGTCGGTGT

GGGCTGCGTCCTGGATGGGGTGCGCTACAACAACGGCCAGTCCTTCCAGC

CTAACTGCAAGTACAACTGCACGTGCATCGACGGCGCGGTGGGCTGCACA

CCACTGTGCCTCCGAGTGCGCCCCCCGCGTCTCTGGTGCCCCCACCCGCG

GCGCGTGAGCATACCTGGCCACTGCTGTGAGCAGTGGGTATGTGAGGACG

ACGCCAAGAGGCCACGCAAGACCGCACCCCGTGACACAGGAGCCTTCGAT

GCTGTGGGTGAGGTGGAGGCATGGCACAGGAACTGCATAGCCTACACAAG

CCCCTGGAGCCCTTGCTCCACCAGCTGCGGCCTGGGGGTCTCCACTCGGA

TCTCCAATGTTAACGCCCAGTGCTGGCCTGAGCAAGAGAGCCGCCTCTGC

AACTTGCGGCCATGCGATGTGGACATCCATACACTCATTAAGGCAGGGAA

GAAGTGTCTGGCTGTGTACCAGCCAGAGGCATCCATGAACTTCACACTTG

CGGGCTGCATCAGCACACGCTCCTATCAACCCAAGTACTGTGGAGTTTGC

ATGGACAATAGGTGCTGCATCCCCTACAAGTCTAAGACTATCGACGTGTC

CTTCCAGTGTCCTGATGGGCTTGGCTTCTCCCGCCAGGTCCTATGGATTA

ATGCCTGCTTCTGTAACCTGAGCTGTAGGAATCCCAATGACATCTTTGCT

GACTTGGAATCCTACCCTGACTTCTCAGAAATTGCCAACTAGGCAGGCAC

AAATCTTGGGTCTTGGGGACTAACCCAATGCCTGTGAAGCAGTCAGCCCT

TATGGCCAATAACTTTTCACCAATGAGCCTTAGTTACCCTGATCTGGACC

CTTGGCCTCCATTTCTGTCTCTAACCATTCAAATGACGCCTGATGGTGCT

GCTCAGGCCCATGCTATGAGTTTTCTCCTTGATATCATTCAGCATCTACT

CTAAAGAAAAATGCCTGTCTCTAGCTGTTCTGGACTACACCCAAGCCTGA

TCCAGCCTTTCCAAGTCACTAGAAGTCCTGCTGGATCTTGCCTAAATCCC

AAGAAATGGAATCAGGTAGACTTTTAATATCACTAATTTCTTCTTTAGAT

GCCAAACCACAAGACTCTTTGGGTCCATTCAGATGAATAGATGGAATTTG

GAACAATAGAATAATCTATTATTTGGAGCCTGCCAAGAGGTACTGTAATG

GGTAATTCTGACGTCAGCGCACCAAAACTATCCTGATTCCAAATATGTAT

GCACCTCAAGGTCATCAAACATTTGCCAAGTGAGTTGAATAGTTGCTTAA

TTTTGATTTTTAATGGAAAGTTGTATCCATTAACCTGGGCATTGTTGAGG

TTAAGTTTCTCTTCACCCCTACACTGTGAAGGGTACAGATTAGGTTTGTC

CCAGTCAGAAATAAAATTTGATAAACATTCCTGTTGATGGGAAAAGCCCC

CAGTTAATACTCCAGAGACAGGGAAAGGTCAGCCCATTTCAGAAGGACCA

ATTGACTCTCACACTGAATCAGCTGCTGACTGGCAGGGCTTTGGGCAGTT

GGCCAGGCTCTTCCTTGAATCTTCTCCCTTGTCCTGCTTGGGTTCATAGG

AATTGGTAAGGCCTCTGGACTGGCCTGTCTGGCCCCTGAGAGTGGTGCCC

TGGAACACTCCTCTACTCTTACAGAGCCTTGAGAGACCCAGCTGCAGACC

ATGCCAGACCCACTGAAATGACCAAGACAGGTTCAGGTAGGGGTGTGGGT

CAAACCAAGAAGTGGGTGCCCTTGGTAGCAGCCTGGGGTGACCTCTAGAG

CTGGAGGCTGTGGGACTCCAGGGGCCCCCGTGTTCAGGACACATCTATTG

CAGAGACTCATTTCACAGCCTTTCGTTCTGCTGACCAAATGGCCAGTTTT

CTGGTAGGAAGATGGAGGTTTACCAGTTGTTTAGAAACAGAAATAGACTT

AATAAAGGTTTAAAGCTGAAGAGGTTGAAGCTAAAAGGAAAAGGTTGTTG

TTAATGAATATCAGGCTATTATTTATTGTATTAGGAAAATATAATATTTA

CTGTTAGAATTCTTTTATTTAGGGCCTTTTCTGTGCCAGACATTGCTCTC

AGTGCTTTGCATGTATTAGCTCACTGAATCTTCACGACAATGTTGAGAAG

TTCCCATTATTATTTCTGTTCTTACAAATGTGAAACGGAAGCTCATAGAG

GTGAGAAAACTCAACCAGAGTCACCCAGTTGGTGACTGGGAAAGTTAGGA

TTCAGATCGAAATTGGACTGTCTTTATAACCCATATTTTCCCCCTGTTTT

TAGAGCTTCCAAATGTGTCAGAATAGGAAAACATTGCAATAAATGGCTTG

ATTTTTTA
```

Another example amino acid sequence of WISP1 is:

```
                                (SEQ ID NO: 3; mouse WISP1)
MRWLLPWTLAAVAVLRVGNILATALSPTPTTMTFTPAPLEETTTRPEFC

KWPCECPQSPPRCPLGVSLITDGCECCKICAQQLGDNCTEAAICDPHRG
```

LYCDYSGDRPRYAIGVCAQVVGVGCVLDGVRYTNGESFQPNCRYNCTCI

DGTVGCTPLCLSPRPPRLWCRQPRHVRVPGQCCEQWVCDDDARRPRQTA

LLDTRAFAASGAVEQRYENCIAYTSPWSPCSTTCGLGISTRISNVNARC

WPEQESRLCNLRPCDVDIQLHIKAGKKCLAVYQPEEATNFTLAGCVSTR

TYRPKYCGVCTDNRCCIPYKSKTISVDFQCPEGPGFSRQVLWINACFCN

LSCRNPNDIFADLESYPDFEEIAN

Another example polynucleotide sequence encoding WISP1 is:

(SEQ ID NO: 4; mouse WISP1)
TGCAGGGCTAGTCTGTTGGCCTGACGTCAGATGTCGCTTTGACAAACGC

CCCCGGGGGCTGAGGAAGGCTCTCCGCTGCTCTGATGGGCCAGCCCAGT

CCTGGCCCAGCTCCCTGGAGAGGCATCCGCATCCTCTGGGCTGAGCCGT

AGCTCCTGTGACGCTGACTTCCAGGCATGAGGTGGCTCCTGCCCTGGAC

GCTGGCAGCCGTGGCAGTCCTGAGGGTGGGCAACATCCTGGCCACGGCC

CTCTCTCCAACCCCCACAACAATGACCTTCACCCCAGCACCACTAGAGG

AAACGACTACACGCCCCGAATTCTGCAAGTGGCCATGTGAGTGCCCACA

ATCCCCACCTCGCTGCCCACTGGGCGTCAGCCTAATCACAGATGGCTGT

GAATGCTGTAAGATATGTGCCCAGCAGCTTGGGGACAACTGCACAGAGG

CTGCCATCTGTGACCCACACCGGGGCCTCTACTGCGATTACAGTGGGGA

TCGCCCGAGGTACGCAATAGGAGTGTGTGCACAGGTGGTCGGTGTGGGC

TGTGTCCTGGATGGCGTACGCTACACCAATGGCGAGTCCTTCCAACCCA

ACTGCAGGTACAACTGTACCTGCATTGATGGCACGGTGGGCTGCACACC

GCTGTGCCTAAGCCCCAGGCCCCCACGCCTCTGGTGCCGCCAGCCCCGG

CACGTGAGAGTCCCTGGCCAGTGCTGTGAGCAGTGGGTGTGTGATGATG

ACGCAAGGAGACCACGCCAGACTGCACTGTTGGACACCAGAGCCTTTGC

AGCGTCAGGCGCCGTGGAGCAACGGTATGAGAACTGCATAGCCTACACT

AGTCCCTGGAGCCCCTGCTCTACCACCTGTGGCCTAGGTATCTCCACTC

GGATCTCTAACGTCAATGCCCGGTGCTGGCCAGAGCAGGAAAGTCGCCT

CTGCAACCTGCGGCCATGTGATGTGGACATCCAACTACACATCAAGGCA

GGGAAGAAATGCCTGGCTGTGTACCAGCCAGAGGAGGCCACGAACTTCA

CTCTCGCAGGCTGTGTCAGCACACGCACCTACCGACCCAAGTACTGCGG

AGTCTGTACTGACAATAGGTGTTGCATCCCCTACAAGTCCAAGACCATC

AGTGTGGATTTCCAGTGTCCAGAGGGGCCAGGTTTCTCCCGGCAGGTCC

TATGGATTAATGCTTGCTTCTGCAACCTGAGCTGCAGGAATCCTAACGA

TATCTTTGCTGACTTGGAATCTTACCCTGACTTCGAAGAGATTGCCAAT

TAGGTGGGTGTGTGGCTCAGGGTAAAGTTCCATGCTGCAAAGCAGCCAG

CCCTTTGTGGTCCAGGACTTCACAATTGAGCCTTATTTCATCTACTTCC

TACTCGATTCTGAATTCCCAGTTTCTGTTCCTGTTTTGACAATCGTAAT

GGCCCAGGAGAGTGCTGCTCAGGCTCAGACAATGGGTTCCTCCTTGGGG

ACATTCTACATCATTCCAAGGAAAACACATCTCTGACTGTTCACAATGG

AAGCAAAGCCTGGCCCAGCTAGTCTGGCTCCAGCCTGGGCAAGTTGTCA

GAAGTTGTGATGGGATTGTCCAAGGAAAAGCATCAGCTGAAGAACCAGT

ATCATGAAGTCCTTCCTCAGATGCCAAGCCTAGGGATGCTGGGATCCTT

TCAGACAGATGGATGGGATTGGGGACACAGGAATAAGCTATTATTTTAC

CCTTGCCAAATGATACTATCCTGGGTATTTCTGCCTAAAACATACCAAA

AGTGTTCTTGTTCCACTGATCTGTATATCACAAGTCACCAAACATTTTC

CAGGTGAGGACCATAGTTGTGTCATTCTGTTTTGCTATTGAAAATCATT

TTAAAAGAAGGAAAAAAAAAAAGAAAAGAAAAGAAAGTCATTTCATT

AACTTGGGCACTTTCTCCTCTCACCCCATATTCTATAAAGGGCTAAACT

TGGGTTCTTGTTGATCAGGAATGTAATTTGAGAAGTCTTACTTTTGCAG

GGAGATGGTAGCCCTCAATTCATCCCGTAGGGATGGGACAAGGCCAGCC

AATCTTTCAAGCCATAGCTGGGCAGGTCACTGAATCTGCTGCTGGCCAA

GTTCTTAGGACAATTAGCCAAAATCTGGGCCTCTCTCTCCCTAGGGTTC

ATGGGAGTTGGTAGGGACCGTAGAGTGACTTGTCTGTTGTCTCAAAAAG

TAAGATGGAAAGATGTTCTCATGGCCCTTAGAAGACTCTTTTGAAGTCT

ACGCCAGACCTAACAGAATATGTGCATCAAACAAACAAGTGGATCACCC

TCCCATGGCCTGGGTGACCTCTAGCAGTCACCCAGTGACTGTGGTAAGG

CCACAGTAGTCCCTGGACCCAGGACAAATCTTTTTTGTTTCAGTGACCT

ACTTTACAGCCTCAGTGTCTATGAAGAAAGTTAACTCAGTTTTCTCATC

TGAAGACAGAAGTCGACCAGCCATTCAGAAATGGGGATCTATTTAGTAG

TGGTAAACGTTAAAGAGTTTGTAAGCTAAAGAAATATTTTTTTTCCTAA

GTGATAATGAGGTTGTTACCTATTTTAGAGGTAGAATTTTCTGTCATCA

TCCTTTTATTGTGTTCTACATACTACCCATTGTTCTCAATATTTGCCAC

ACATTTACTCATTGAAACTTGCTGATAACACAGAGGACTTCCCTTAATG

ATTTCTGTTCTTGACACTGTGAAATATCAATTCAAAGAGGCTAATAAGT

TCAATCAAAGTCACCTATCTGAAGACTCATAGCCAGAGAAGATTGCCTT

CATATTTCCCCTTTGCTTCTGGACCTTGTAAACATGTCAGGGCAGGAAA

GCATACAGAAGTCAGCAGCTTGCCCTCTTAGTATTGGCTCTCTAGCCCC

TTTCACGTAAGAGGAGAGTGTGTCTAGGTACTAAGGATCCAACCTAAAC

TGGACAGAAAAGGGCATGTGCATTATCCCCTGTGGCTCCTCCTGCCCTG

GAATCAGAACTAGCTTACAGCATGCTTTTATATGATGATTCAGTTTGCC

CCACACCATACATATGGGCATATGGGAGAACTATACACACACTCATAAA

TGGATTTGTAAGTAGGAAAGGGGACTTGAGATTTCCCCTCCTTCCTGCA

ACTTCCCAAAGGCCTGGCCTTATGCAAGGCAAACAGTGGTGCTTAAGAT

GTATTTTGGGAAGAAAATACTATATATATATATTCCTATTTTTCCTTAG

AAGCCTTTTCTTCCAGGATCTCATCTTAACAGTAAGAAATCCTCTCTTA

AGAGAGGCCTAGTATTTTGAGTAAACATATGTTCATATGTGTACAAGTA

CTTGTATGTAAATATAAGTTACCACTGTGGGTTATTAATTAGGTAAATT

TTATGTGGTATCATATTTGATTTTCTTCTATTGGAAAAATCTGCCTTAA

CAGCTAACTCTGTAAGAACTTCCATAGGAGCCATAAGCTAGGGTCTTCC

CAGGTATCCATCCTCTTTTGGGAAACTGAGCTGAGCATCTTCAACCAAA

-continued

```
GGAGTTAGGGTGATCATTGGGAATAGGAGAAAGGGATGGCCAGGGTAGC

TCCATCGTTATTTAGAAACAGACCTGGCATACAGAACGACCAGAGGAAC

CAACCTTCTTTGAACCAAGGGAAAAAGACTTGGATGTAATATATAGAAG

CTTTTTCTAATAGTCAGAAACAGACTTTAATTGTATGGCCTGGTTCAAG

GAAAGTTAAGAATGTCCATTATCGTTAAAAACAAAAGTCCATTATTGAT

AGCTTATTTGGTGCTAAGCCCTACGGTGCATTTTGTCCGGCTATCACTT

AGCAGAGCCATGCTCAGTACACAGTCTTTCTCTATTCAATAAATAGAAA

CGCTGAAGCTCAAAGGCACTGAGGAGCTGAGGCTCAGAAGCATGTTTAG

TCCACTCTATCAGGGGGGAAGAGATCTTGACGGAACCTAAATGACTAC

TATTGGAAACTCATATTTGAAAGCTTTCAGAAGTCCCACCCCCACCCCA

TCCCCAGATGCTTAGAAACTAAAGAAGCAATGAGGATGAGCTAGCCTTC

AGTGAAGAGGTTCACTACTGCACCAAGAGTGAATGTCTTAGGTGTACTT

AGTCATTGGACAGGGAGACCTGAGTGAGTTTGTGAACCTGCAGCTTACT

AAACCTTACAATGAGCATTTGGAGAGCCAAGACTGCTTCTCGGCGCTTT

ACTGACATGGCTTGCTTAATCTTCTCAGTGAGCCCAAGAGTCAGGGCGT

TACCACTGCCCATTTTAGGGCTGAGAAAGCAAAATCTCCAGGAGTTAAG

TGATTTGCTCAAGTTTTTAACCAACCGAGGCACTGCAGATAAACTCCGA

AGCCCAGTGTCATGTAACATGCCCATGCCATCTCTCCGGACACGCAGCC

CATTTTCCTGTTCCTAAACCAAAGGCTCAGAGTCACCAGAACCAACTCA

CAGGACAGTGCAGAAATTCTAATGTCGAGGGTGATTAGAGACTGATCAA

AGAAAGTAATTTCAAATGATATGATTGTTTGTAAGCACCCTAGTTAATT

CTGGACTACATATGCATAGAGATTGTGAAGAACATTACAGCCTGTGACT

ATAACGTTGACTTCTGTCATTTCTTTTTAAAGACTTGTTTTTTTTTTTT

TACTCAAAGGACCCACAGTGACAGCCCTGAATGGTTGAGAAGCATTGAT

TAGCTGTGAGTCCTGCATATGTATGTATGTGTGTGTGTGTGTGTATT

TGTATGTACTTATCTATTTTCAAACTGTGATTGTGTATTTAAATATTCC

TCCTGCCATTTTGTAAGTGATTACGCATAAAGAAACACCTTTGAATGTC

CTAATAAAGGAGAGCTAGCCCTTGGGCGGCCTGTCACATTTTGCCACTT

TCCTCATTTTTCTCATGATCTGTGTAGCAGGGAATGTGTTTGTTCAACC

ATGATGAGTTTTCATTGTTCAAATTCTTTGTTTACAGCTTTTCTCCTTA

AAGCAATAAATCATCAGCAACAGT
```

The WISP1 N-terminal domain shares homology with insulin-like growth factor binding proteins (IGFB), but it has been reported that recombinant human IGF has very low affinity to human CTGF (Vorwerk, P. et al. (2002) Endocrinology 143: 1677-85).

The N-terminal domain is followed by a cysteine-rich (CR) domain, also known as a Von Willebrand Factor C (VWC) repeat. The CCN VWC domain has been shown to interact with bone morphogenic proteins (BMPs) and transforming growth factor β (TGF-β) (Abreu, J. G. et al. (2002) Nat. Cell Biol. 4: 599-604). In particular, it was reported that the *Xenopus laevis* CTGF could antagonise BMP4 activity by blocking its binding to the receptor, while it could bind to TGF-β1 and potentiate binding to its receptor and thus the downstream signalling (Abreu, J. G. et al. (2002) Nat. Cell Biol. 4: 599-604). In addition, the CCN1 and CCN2 members of the matricellular proteins have been shown to interact with integrins αvβ3, αvβ1 as well as heparin sulfate proteoglycan also via their CR domains, translating to pro-angiogenic activities of endothelial cells or adhesion of hepatic cells (Chen, N. et al. (2004) J. Biol. Chem. 279: 44166-76; Leu, S. J. et al. (2002) J. Biol. Chem. 277: 46248-55; Gao, R. et al. (2004) J. Biol. Chem. 279: 8848-55; Kawaki, H. et al. (2008) J. Bone Miner. Res. 23: 1751-64). It was further suggested in chondrocytes that CCN2 binding to aggrecan through both IGFBP and VWC domains could elicit aggrecan release (Aoyama, E. et al. (2009) Biochem. J. 420: 413-20).

The third functional domain is a Type-1 thrombospondin repeat (TSP). Numerous targets have been reported to bind to TSP1 domains in a range of proteins, such as integrin αvβ1 (Leu, S. J. et al. (2003) J. Biol. Chem. 278: 33801-8), fibronectin (Sipes, J. M. et al. (1993) J. Cell Biol. 121: 469-77), collagen V (Takagi, J. et al. (1993) J. Biol. Chem. 268: 15544-9), CD36 (Asch, A. S. et al. (1992) Biochem. Biophys. Res. Commun. 182: 1208-17), TGF-β (Schultz-Cherry, S. et al. (1995) J. Biol. Chem. 270: 7304-10) and heparin (Guo, N. H. et al. (1992) J. Biol. Chem. 267: 19349-55). However, the CCN targets binding to the TSP1 domains are less characterised (Holbourn, K. P. et al. (2008) Trends Biochem. Sci. 33: 461-73). It has been demonstrated that CCN2 interacts with VEGF-A through its TSP1 domain, and it has been suggested that metalloproteases may interact with the same domain (Hashimoto, G. et al. (2002) J. Biol. Chem. 277: 36288-95; Inoki, I. et al. (2002) FASEB J. 16: 219-21); but direct evidence of CCN TSP1 domain interactions with suggested targets remain to be established.

The C-terminal domain of the CCN members possesses a cysteine knot motif. This CT domain was shown to interact with LRP-6, fibronectin, perlecan and fibulin-1 in CCN2 (Mercurio, S. et al. (2004) Development 131: 2137-47; Nishida, T. et al. (2003) J. Cell Physiol. 196: 265-75; Perbal, B. et al. (1999) Proc. Natl. Acad. Sci. USA 96: 869-74).

In addition to the full length WISP1, a number of WISP1 splice variants are known.

An example amino acid sequence of a WISP1 splice variant lacking the VWC, TSP1 and CT domains is:

```
                                        (SEQ ID NO: 5)
MRWFLPWTLAAVTAAAASTVLATALSPAPTTMDFTPAPLEDTSSRPQFCK

WPCECPPSPPRCPLGVSLITDGCECCKMCAQQLGDNCTEAVICDPHRGLY

CDYSGDRPRYAIGVCARREEVSGCVPARGIHELHTCGLHQHTLLSTQVLW

SLHGQQVLHPLQV
```

An example polynucleotide sequence encoding a WISP1 splice variant lacking the VWC, TSP1 and CT domains is:

```
                                        (SEQ ID NO: 6)
CCGAGAGGTGGTCGGATCCTCTGGGCTGCTCGGTCGATGCCTGTGCCACT

GACGTCCAGGCATGAGGTGGTTCCTGCCCTGGACGCTGGCAGCAGTGACA

GCAGCAGCCGCCAGCACCGTCCTGGCCACGGCCCTCTCTCCAGCCCCTAC

GACCATGGACTTTACCCCAGCTCCACTGGAGGACACCTCCTCACGCCCCC

AATTCTGCAAGTGGCCATGTGAGTGCCCGCCATCCCCACCCCGCTGCCCG

CTGGGGGTCAGCCTCATCACAGATGGCTGTGAGTGCTGTAAGATGTGCGC
```

-continued
TCAGCAGCTTGGGGACAACTGCACGGAGGCTGTCATCTGTGACCCCACC

GGGGCCTCTACTGTGACTACAGCGGGGACCGCCCGAGGTACGCAATAGGA

GTGTGTGCACGCAGGGAAGAAGTGTCTGGCTGTGTACCAGCCAGAGGCAT

CCATGAACTTCACACTTGCGGGCTGCATCAGCACACGCTCCTATCAACCC

AAGTACTGTGGAGTTTGCATGGACAACAGGTGCTGCATCCCCTACAAGTC

TAAGACTATCGACGTGTCCTTCCAGTGTCCTGATGGGCTTGGCTTCTCCC

GCCAGGTCCTATGGATTAATGCCTGCTTCTGTAACCTGAGCTGTAGGAAT

CCCAATGACATCTTTGCTGACTTGGAATCCTACCCTGACTTCTCAGAAAT

TGCCAACTAGGCAGGC

An example amino acid sequence of a WISP1 splice variant lacking the IGFB and VWC domains is:

(SEQ ID NO: 7)
MPVPLTSRHEVVPALDAGSSDSSRQHRPGHDAVGEVEAWHRNCIAYTSP

WSPCSTSCGLGVSTRISNVNAQCWPEQESRLCNLRPCDVDIHTLIKAGKK

CLAVYQPEASMNFTLAGCISTRSYQPKYCGVCMDNRCCIPYKSKTIDVSF

QCPDGLGFSRQVLWINACFCNLSCRNPNDIFADLESYPDFSEIAN

An example polynucleotide sequence encoding a WISP1 splice variant lacking the IGFB and VWC domains is:

(SEQ ID NO: 8)
CCGAGAGGTGGTCGGATCCTCTGGGCTGCTCGGTCGATGCCTGTGCCACT

GACGTCCAGGCATGAGGTGGTTCCTGCCCTGGACGCTGGCAGCAGTGACA

GCAGCAGCCGCCAGCACCGTCCTGGCCACGATGCTGTGGGTGAGGTGGAG

GCATGGCACAGGAACTGCATAGCCTACACAAGCCCCTGGAGCCCTTGCTC

CACCAGCTGCGGCCTGGGGGTCTCCACTCGGATCTCCAATGTTAACGCCC

AGTGCTGGCCTGAGCAAGAGAGCCGCCTCTGCAACTTGCGGCCATGCGAT

GTGGACATCCATACACTCATTAAGGCAGGGAAGAAGTGTCTGGCTGTGTA

CCAGCCAGAGGCATCCATGAACTTCACACTTGCGGGCTGCATCAGCACAC

GCTCCTATCAACCCAAGTACTGTGGAGTTTGCATGGACAATAGGTGCTGC

ATCCCCTACAAGTCTAAGACTATCGACGTGTCCTTCCAGTGTCCTGATGG

GCTTGGCTTCTCCCGCCAGGTCCTATGGATTAATGCCTGCTTCTGTAACC

TGAGCTGTAGGAATCCCAATGACATCTTTGCTGACTTGGAATCCTACCCT

GACTTCTCAGAAATTGCCAACTAGGCAGGC

An example amino acid sequence of a WISP1 splice variant consisting of only the CT domain is:

(SEQ ID NO: 9)
MRWFLPWTLAAVTAAAASTVLATAGKKCLAVYQPEASMNFTLAGCISTRS

YQPKYCGVCMDNRCCIPYKSKTIDVSFQCPDGLGFSRQVLWINACFCNLS

CRNPNDIFADLESYPDFSEIAN

An example polynucleotide sequence encoding a WISP1 splice variant consisting of only the CT domain is:

(SEQ ID NO: 10)
GCGTCCGCTGGGCCCAGCTCCCCCGAGAGGTGGTCGGATCCTCTGGGCTG

CTCGGTCGATGCCTGTGCCACTGACGTCCAGGCATGAGGTGGTTCCTGCC

CTGGACGCTGGCAGCAGTGACAGCAGCAGCCGCCAGCACCGTCCTGGCCA

CGGCAGGGAAGAAGTGTCTGGCTGTGTACCAGCCAGAGGCATCCATGAAC

TTCACACTTGCGGGCTGCATCAGCACACGCTCCTATCAACCCAAGTACTG

TGGAGTTTGCATGGACAACAGGTGCTGCATCCCCTACAAGTCTAAGACTA

TCGACGTGTCCTTCCAGTGTCCTGATGGGCTTGGCTTCTCCCGCCAGGTC

CTATGGATTAATGCCTGCTTCTGTAACCTGAGCTGTAGGAATCCCAATGA

CATCTTTGCTGACTTGGAATCCTACCCTGACTTCTCAGAAATTGCCAACT

AGGCAGGCACAAATCTTGGGTCTTGGGGACTAACCCAATGCCTGTGAAGC

AGTCAGCCCTTATGGCCAATAACTTTTCACCAATGAGCCTTAGTTACCCT

GAAAAAAAAAAAAAAAAAAAAAA

Muscle Function and Mass

The compounds, compositions, uses and methods disclosed herein may provide for the maintenance of or increase in muscle function and/or mass.

The term "muscle function" refers to the ability of a muscle to perform in a manner that does not negatively impact on the life of a subject, and encompasses parameters of muscle strength, muscle contraction, muscle endurance and/or muscle elasticity.

Suitable tests for assessing muscle function include grip strength assessment using a dynamometer; one repeat maximum on leg press, chest press or leg extension; gait speed; 6 min walk test; time up and go; short physical performance battery; Fried frailty criteria; and stair climbing time assessments.

Muscle mass (which may equate with muscle volume, muscle thickness or myofiber size) may be measured by dual-energy X-ray absorptiometry (DXA) or bioimpedance tests. Similarly, MRI may be used for assessing muscle volume and ultra-sound may be used for assessing muscle thickness and pennation angle.

"Muscle wasting" may be a reduction in muscle mass, for example to the stage where the muscle loss becomes debilitating. In one embodiment, the subject does not lose more than 10%, 5%, 4%, 3%, 2% or 1% of their muscle mass.

Preferably, the compounds, compositions, uses and methods disclosed herein provide for the maintenance of or increase in muscle mass.

The term "maintains" refers to a particular parameter, such as muscle function and/or mass, remaining substantially unchanged over a period of time (e.g. 5, 10, 15, 20, 25, 30, 40, 50 or more years).

In one embodiment, muscle mass increases by at least 1%, 2%, 3%, 4%, 5%, 10%, 15% or 20%.

In another embodiment, muscle mass increases by 1-2.5%, 1-5%, 1-10% or 1-20%.

Preferably, the muscle is skeletal muscle.

Sarcopenia and Frailty

The invention provides a means to address loss of muscle function and mass that occurs with age. Age-related loss of muscle function and mass occurs inevitably in all individuals, however its progression depends on a range of genetic and environmental factors, such as physical activity and nutritional intake.

The specific condition of sarcopenia is defined as occurring at the point at which the age-related loss of muscle mass and function becomes debilitating and impacts on quality of life (Sayer, A. A. et al. (2013) Age Ageing 42: 145-150). In contrast, frailty is a classification of age-related muscle dysfunction which relies on muscle strength and functionality, but not muscle mass (Morley, J. E. et al. (2013) J. Am. Med. Dir. Assoc. 14: 392-397).

Sarcopenia and frailty are multi-factorial syndromes which associate with pathophysiological changes, such as impaired neuro-muscular transition, altered excitation/contraction coupling, impaired regenerative capacity linked to stem cell exhaustion, defects of mitochondrial and energy metabolism in myofibers, and marbling of skeletal muscle with fat and fibrosis (Ali, S. et al. (2014) Gerontology 60: 294-305). The aetiology of these syndromes is therefore complex and poorly understood, but low physical activity, hormonal decline in anabolic hormones (e.g. androgens and IGF-1), and malnutrition and/or nutritional deficiencies play an important role (Mithal, A. et al. (2013) Osteoporos. Int. 24: 1555-1566).

Muscle Injury

In an experimental setting (e.g. in mice), muscle damage is commonly induced by an intramuscular injection of either snake venom toxins or glycerol. These intramuscular injections induce acute muscle degeneration within the first 3 days after muscle injury. This procedure models what occurs during natural muscle injury.

Acute muscle degeneration is characterised by a strong destruction of the muscle fibres, and an infiltration of immune cells into the muscle. The role of the immune response during muscle regeneration is critical and has to be properly coordinated. Neutrophils and pro-inflammatory macrophages first invade the muscle and participate in the clearance of muscle debris post-injury. The immune cell population then switches to anti-inflammatory macrophages which sustain muscle regeneration. The sequential secretion of cytokines by immune cells is thus finely orchestrated during the first few days after muscle injury and modulates the activity of the muscle progenitors. Indeed, numerous muscle-resident progenitor cells start to activate and proliferate once the muscle debris has been cleared, and will soon engage into specific lineage commitment to regenerate the muscle. In particular, the muscle stem cells (satellite cells, SATs) proliferate and eventually differentiate into muscle fibres. Mesenchymal non-myogenic progenitor cells, or fibro/adipogenic progenitors (FAPs) are also activated at the same time in order to sustain myogenesis. 7 days after muscle injury, most progenitor populations have committed, and the immune response has been resolved. By 14 days after injury, the muscle is composed of newly formed myofibers and most signals have returned to basal level.

The compounds, compositions, uses and methods disclosed herein may be used for treating, preventing or reducing the detrimental effects of muscle injury. While not wishing to be bound by theory, the WISP1 or fragments or variants thereof disclosed herein appear to increase muscle regeneration (e.g. by promoting muscle stem cell function).

In one embodiment, the subject has incurred muscle injury through a surgical intervention and/or trauma.

The term "surgical intervention" refers to any surgical approach that results in damage to muscle. Thus, the compounds, compositions, uses and methods disclosed herein may be used in aiding recovery after a surgical procedure.

The term "trauma" as used herein refers to an unplanned event that results in injury of a muscle, for example an accident or sporting injury.

In another embodiment, the subject is to undergo a planned surgical intervention. For example, the compounds, compositions, uses and methods disclosed herein may be applied to a subject who is scheduled to undergo surgery in less than 1 month, or less than 3, 2 or 1 weeks.

In another embodiment, the subject has incurred muscle damage or rhabdomyolysis as a side effect of chemical exposure to toxins or drugs, for example, from cholesterol-lowering drugs such as statins.

Method of Treatment

It is to be appreciated that all references herein to treatment include curative, palliative and prophylactic treatment; although in the context of the invention references to preventing are more commonly associated with prophylactic treatment. Treatment may also include arresting progression in the severity of a disease.

Subject

The treatment of mammals, particularly humans, is preferred. However, both human and veterinary treatments are within the scope of the invention.

For veterinary subjects, equine subjects are preferred.

The ageing subject to be treated may be, for example, a human subject over the age of 30, 35, 40, 45, 50, 55, 60, 65, 70, 75, 80, 85, 90, 95 or 100 years old. For veterinary applications, the age of the animal would be scaled from the human situation using the average lifespan for calibration.

Method of Screening

In one aspect, the invention provides method of screening for an agent capable of increasing Wnt-inducible signalling protein 1 (WISP1) levels in a subject. The method may comprise the steps:

(a) contacting a population of cells with a candidate agent;

(b) determining the level of WISP1 in the population of cells; and (c) comparing the level of WISP1 determined in step (b) with a WISP1 level in a control population of cells which has not been contacted with the candidate agent.

Preferably, the method is an in vitro method.

The candidate agent may, for example be a pharmaceutical agent or nutritional supplement. Preferably, the candidate agent is a nutritional supplement. The term "nutritional supplement" refers to a product which is intended to supplement the general diet of a subject.

In one embodiment, the candidate agent is comprised in a library of candidate agents.

In one embodiment, the population of cells is a population of muscle cells (e.g. the C2C12 cell line and/or human primary myoblasts). The population of muscle cells may be, for example, a population of muscle stem and/or progenitor cells (e.g. satellite (SAT) and/or fibro/adipogenic progenitor (FAP) cells).

The term "level of WISP1" refers to the amount of WISP1 protein that is found in a sample. The amount of WISP1 protein may be determined directly or indirectly. Direct methods of determining WISP1 include SDS-PAGE, Western blotting, chromatographic methods (e.g. HPLC or FPLC), mass spectrometry-based methods (e.g. LC/MS) and NMR. Indirect methods of determining WISP1 include methods based on the detection of WISP1-encoding polynucleotides, in particular mRNAs, such as qPCR.

The effect of the candidate agent on WISP1 levels may be assessed as a function of time, by carrying out repeated measurements over a particular time-course.

For example, candidate agents may include, Wnt ligands or Frizzled agonists.

Method of Diagnosis

In one aspect, the invention provides a method of diagnosing sarcopenia or frailty comprising the steps:
  (a) providing a biological sample isolated from a subject;
  (b) determining the level of Wnt-inducible signalling protein 1 (WISP1) in the biological sample; and
  (c) comparing the level of WISP1 determined in step (b) with a WISP1 level determined from one or more control samples or reference levels.

The one or more control samples may be isolated from a subject with or without sarcopenia or frailty. Accordingly, comparison with such control samples may provide an indication of the subject having sarcopenia or frailty, or deteriorating towards the state of sarcopenia or frailty.

Alternatively or additionally, a level of WISP1 below a pre-determined reference level may indicate the subject has sarcopenia or frailty, while a level of WISP1 above a pre-determined reference level may indicate the subject does not have sarcopenia or frailty.

The term "level of WISP1" refers to the amount of WISP1 protein that is found in a sample. The amount of WISP1 protein may be determined directly or indirectly. Direct methods of determining WISP1 include SDS-PAGE, Western blotting, chromatographic methods (e.g. HPLC or FPLC), mass spectrometry-based methods (e.g. LC/MS) and NMR. Indirect methods of determining WISP1 include methods based on the detection of WISP1-encoding polynucleotides, in particular mRNAs, such as qPCR.

The biological sample may be any suitable sample for isolating from the body of a subject, such as a blood sample (e.g. plasma or serum) or tissue biopsy (in particular a muscle biopsy).

In one embodiment, the method may comprise a further step of administering the WISP1 or fragment or variant thereof disclosed herein to the subject, wherein the subject has been diagnosed as having sarcopenia or being at risk of developing sarcopenia, or diagnosed as being frail or at being at risk of becoming frail.

In another embodiment, the method may comprise a further step of applying a dietary intervention for maintaining or increasing muscle function and/or mass wherein the subject has been diagnosed as having sarcopenia or being at risk of developing sarcopenia, or diagnosed as being frail or being at risk of becoming frail. Preferably, the dietary intervention is for maintaining or increasing muscle mass. Example dietary interventions include high protein and/or carbohydrate diets.

In another aspect, the invention provides a method of diagnosing loss of muscle function and/or mass (e.g. with age) comprising the steps:
  (a) providing a biological sample isolated from a subject;
  (b) determining the level of Wnt-inducible signalling protein 1 (WISP1) in the biological sample; and
  (c) comparing the level of WISP1 determined in step (b) with a WISP1 level determined from one or more control samples or reference levels.

The loss of muscle function and/or mass may be associated with sarcopenia or frailty.

In another aspect, the invention provides a method of selecting a dietary intervention comprising the steps:
  (a) providing a biological sample isolated from a subject;
  (b) determining the level of Wnt-inducible signalling protein 1 (WISP1) in the biological sample;
  (c) comparing the level of WISP1 determined in step (b) with a WISP1 level determined from one or more control samples or reference levels; and
  (d) applying a dietary intervention for maintaining or increasing muscle function and/or mass wherein the subject has been diagnosed as having sarcopenia or being at risk of developing sarcopenia, or diagnosed as being frail or being at risk of becoming frail.

Preferably, the dietary intervention is for maintaining or increasing muscle mass. Example dietary interventions include high protein and/or carbohydrate diets, and vitamin B12 and/or vitamin D supplements.

A control sample may be from the same subject, taken at an earlier time point. Similarly, a reference level may be determined based on previous analyses carried out on the same subject. Accordingly in another aspect, the invention provides a method of determining the progression of sarcopenia or frailty in a subject comprising the steps:
  (a) providing a biological sample isolated from a subject;
  (b) determining the level of Wnt-inducible signalling protein 1 (WISP1) in the biological sample; and
  (c) comparing the level of WISP1 determined in step (b) with a WISP1 level determined from a sample taken from the same subject at an earlier time.

Dietary Intervention and Product

The term "dietary intervention" refers to an external factor applied to a subject which causes a change in the subject's diet. In one embodiment, the dietary intervention is a high calorie diet. In another embodiment, the dietary intervention is a high protein and/or carbohydrate diet. In another embodiment, the dietary intervention is a diet supplemented with vitamins and minerals, in particular vitamin B12 and/or vitamin D.

The diet may be one which is adjusted to the starting body weight of the subject.

The dietary intervention may comprise administration of at least one diet product. The diet product may be a meal replacement product or a supplement product which may, for example, increase the subject's appetite. The diet product may include food products, drinks, pet food products, food supplements, nutraceuticals, food additives or nutritional formulae. Example oral nutritional supplements include Nestle Boost and Meritene products.

Variants, Derivatives, Analogues, Homologues and Fragments

In addition to the specific proteins and nucleotides mentioned herein, the invention also encompasses the use of variants, derivatives, analogues, homologues and fragments thereof.

In the context of the invention, a variant of any given sequence is a sequence in which the specific sequence of residues (whether amino acid or nucleic acid residues) has been modified in such a manner that the polypeptide or polynucleotide in question substantially retains its function. A variant sequence can be obtained by addition, deletion, substitution, modification, replacement and/or variation of at least one residue present in the naturally-occurring protein.

The term "derivative" as used herein, in relation to proteins or polypeptides of the invention includes any substitution of, variation of, modification of, replacement of, deletion of and/or addition of one (or more) amino acid residues from or to the sequence providing that the resultant protein or polypeptide substantially retains at least one of its endogenous functions.

The term "analogue" as used herein, in relation to polypeptides or polynucleotides includes any mimetic, that is, a chemical compound that possesses at least one of the endogenous functions of the polypeptides or polynucleotides which it mimics.

Typically, amino acid substitutions may be made, for example from 1, 2 or 3 to 10 or 20 substitutions provided that the modified sequence substantially retains the required activity or ability. Amino acid substitutions may include the use of non-naturally occurring analogues.

Proteins used in the invention may also have deletions, insertions or substitutions of amino acid residues which produce a silent change and result in a functionally equivalent protein. Deliberate amino acid substitutions may be made on the basis of similarity in polarity, charge, solubility, hydrophobicity, hydrophilicity and/or the amphipathic nature of the residues as long as the endogenous function is retained. For example, negatively charged amino acids include aspartic acid and glutamic acid; positively charged amino acids include lysine and arginine; and amino acids with uncharged polar head groups having similar hydrophilicity values include asparagine, glutamine, serine, threonine and tyrosine.

Conservative substitutions may be made, for example according to the table below. Amino acids in the same block in the second column and preferably in the same line in the third column may be substituted for each other:

| ALIPHATIC | Non-polar | G A P |
| | | I L V |
| | Polar-uncharged | C S T M |
| | | N Q |
| | Polar-charged | D E |
| | | K R H |
| AROMATIC | | F W Y |

The term "homologue" as used herein means an entity having a certain homology with the wild type amino acid sequence and the wild type nucleotide sequence. The term "homology" can be equated with "identity".

A homologous sequence may include an amino acid sequence which may be at least 50%, 55%, 60%, 65%, 70%, 75%, 80%, 85% or 90% identical, preferably at least 95% or 97% or 99% identical to the subject sequence. Typically, the homologues will comprise the same active sites etc. as the subject amino acid sequence. Although homology can also be considered in terms of similarity (i.e. amino acid residues having similar chemical properties/functions), in the context of the invention it is preferred to express homology in terms of sequence identity.

A homologous sequence may include a nucleotide sequence which may be at least 50%, 55%, 60%, 65%, 70%, 75%, 80%, 85% or 90% identical, preferably at least 95% or 97% or 99% identical to the subject sequence. Although homology can also be considered in terms of similarity, in the context of the invention it is preferred to express homology in terms of sequence identity.

Preferably, reference to a sequence which has a percent identity to any one of the SEQ ID NOs detailed herein refers to a sequence which has the stated percent identity over the entire length of the SEQ ID NO referred to.

Homology comparisons can be conducted by eye or, more usually, with the aid of readily available sequence comparison programs. These commercially available computer programs can calculate percent homology or identity between two or more sequences.

Percent homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion in the nucleotide sequence may cause the following codons to be put out of alignment, thus potentially resulting in a large reduction in percent homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible, reflecting higher relatedness between the two compared sequences, will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum percent homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al. (1984) Nucleic Acids Res. 12: 387). Examples of other software that can perform sequence comparisons include, but are not limited to, the BLAST package (see Ausubel et al. (1999) ibid—Ch. 18), FASTA (Atschul et al. (1990) J. Mol. Biol. 403-410) and the GENEWORKS suite of comparison tools. Both BLAST and FASTA are available for offline and online searching (see Ausubel et al. (1999) ibid, pages 7-58 to 7-60). However, for some applications, it is preferred to use the GCG Bestfit program. Another tool, called BLAST 2 Sequences is also available for comparing protein and nucleotide sequences (see FEMS Microbiol. Lett. (1999) 174: 247-50; FEMS Microbiol. Lett. (1999) 177: 187-8).

Although the final percent homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see the user manual for further details). For some applications, it is preferred to use the public default values for the GCG package, or in the case of other software, the default matrix, such as BLOSUM62.

Once the software has produced an optimal alignment, it is possible to calculate percent homology, preferably percent sequence identity. The software typically does this as part of the sequence comparison and generates a numerical result.

"Fragments" of Wnt-inducible signalling protein 1 (WISP1) are also variants and the term typically refers to a selected region of the polypeptide or polynucleotide that is of interest either functionally or, for example, in an assay. "Fragment" thus refers to an amino acid or nucleic acid sequence that is a portion of a full-length polypeptide or polynucleotide.

Such variants may be prepared using standard recombinant DNA techniques such as site-directed mutagenesis. Where insertions are to be made, synthetic DNA encoding the insertion together with 5' and 3' flanking regions corresponding to the naturally-occurring sequence either side of the insertion site may be made. The flanking regions will contain convenient restriction sites corresponding to sites in the naturally-occurring sequence so that the sequence may be cut with the appropriate enzyme(s) and the synthetic DNA ligated into the cut. The DNA is then expressed in accordance with the invention to make the encoded protein. These methods are only illustrative of the numerous standard techniques known in the art for manipulation of DNA sequences and other known techniques may also be used.

EXAMPLES

Example 1

Materials and Methods
Mice

All mice were housed under standard conditions and allowed access to food and water ad libitum. The strain C57BL/6JRj (Janvier) was used. Young mice were between 9-12 weeks old and aged mice were ≥20 months old.

Muscle regeneration was induced by intramuscular injections of 50 µL of 50% v/v glycerol into tibialis anterior (TA) muscles. Mice were sacrificed 3, 7, 14 or 21 days post injection (dpi) and regenerating TA muscles were analysed at the molecular level. For isolation of muscle progenitors, tibialis anterior, gastrocnemius and quadriceps muscles were intramuscularly injected with 50 µL, 50 µL and 100 µL of 50% v/v glycerol, respectively. Mice were sacrificed 3 days post injection, and muscles were processed for cell isolation by flow-cytometry. For in vivo WISP1 treatment, 1 mg/kg/day of mouse recombinant WISP1 protein was injected intra-peritoneally daily after muscle injury. Control mice were injected with the corresponding volume of PBS.

Rats

All rats were housed under standard conditions and allowed access to food and water ad libitum. The strain WISTAR (Janvier) was used. Rats were sacrificed at 8, 18 or 24 months of age and serum was collected.

Mouse Progenitor Isolation

Muscles were collected uninjured or 3 days after glycerol injection, and digested with Collagenase B and Dispase I.

Cells were incubated at 4° C. for 30 min with CD45-FITC (Invitrogen), CD31-FITC (Invitrogen), CD11b (Invitrogen), CD34-Alexa Fluor 647 (BD Biosciences), CD140a-PE (PDGFRα) (eBioscience), Ly-6A/E-PECy7 (Sca1) (BD Biosciences) and Integrin α7 (R&D).

Satellite cells (SATs) were isolated as: CD31−/CD11b−/CD45−/Sca1−/CD34+/Integrin α7+. Fibro/Adipogenic progenitors (FAPs) were isolated as: CD31−/CD11b−/CD45−/Sca1+/CD34+/PDGFRα+. Lineage positive cells (Lin+) were isolated as: CD31+/CD11b+/CD45+. CD31−/CD11b−/CD45−/Sca1+/CD34+/PDGFRα− cells were also collected and named PDGFRα− cells.

Slow Off+Rate Modified Aptamer Assay (SOMALOGICS)

Muscle samples were pulverised using the cryoPREP impactor system (Covaris). The muscle powder was then subjected to mechanical lysis using a Polytron homogeniser and proteins were extracted in 50 mM Tris (pH 7.5), 150 mM NaCl, 50 mM NaF, 1 mM EDTA, 0.5% TritonX. Protein concentration was determined by a BCA assay and samples were diluted at 250 µg/mL. Rat serum and mouse protein extracts were analysed using DNA aptamer+based recognition on the SOMAscan platform (Somalogic, Boulder, Colo., USA), as described (Gold, L. et al. (2010) PLoS One 5: e15004). Median normalised relative fluorescence units (RFU) were log 2+transformed before applying principal component analysis and linear models. Statistical analyses were performed in R 3.1.3.

Quantitative PCR

RNA was extracted from frozen muscles or freshly sorted cells using miRNeasy Mini Kit or RNeasy Micro Kit (Qiagen), respectively. RNA samples were subjected to reverse transcription using random primers (High Capacity cDNA Reverse Transcription Kit, ABI). Quantitative PCR on full muscle was performed using the SybR Green I master kit (Roche) on a LightCycler 480. Quantitative PCR on isolated progenitors was performed using Taqman® probes (ABI) in combination with the SybR Green I master kit (Roche) on a LightCycler 480.

Satellite Cell Culture

Satellite cells were isolated using Beckman/Coulter Astrios Cell sorter, and were distributed into 96 well plates at a density of 1765 cells/cm$^2$. Freshly sorted satellite cells were grown in high glucose DMEM, 20% heat+inactivated FBS, 10% inactivated horse serum, 2.5 ng/mL bFGF (Invitrogen), 1% penicillin/streptomycin, 1% L+Glutamine, 1% Na+pyruvate (Invitrogen). EdU concentration was 10 µM EdU in the medium for 3 h. Satellite cell differentiation was induced after four days of growth, by switching to differentiation medium (high glucose DMEM, 5% inactivated horse serum, 1% P/S) for 2 days. Cells were treated with WISP1 by addition of mouse recombinant WISP1 protein in the medium, and medium was changed daily.

Human Skeletal Muscle Myoblast (HSMM) Culture

Human skeletal muscle myoblasts (HSMMs) were purchased from Lonza. HSMM cells were seeded at 2000 cells/well in 96-well plates, and grown in HSMM Hamsbio® growth medium for 3 days for proliferation assay. HSMM cells were seeded at 30000 cells/well in 96-well plates, and switched to differentiation medium the following day (DMEM-F12, 2% inactivated FBS, 1% P/S) for 2 days, for differentiation assay.

Immunocytochemistry and Image Analysis

EdU incorporation was revealed using the Click+iT assay (Molecular Probes) according to the manufacturer's instructions. Briefly, cells were fixed for 15 minutes in 4% PFA, permeabilised for 20 minutes in PBTX 0.5%, stained with the Click+iT reaction mix and counterstained with DAPI. For MHC staining, cells were fixed for 10 minutes in 4% PFA, permeabilised using cold EtOH/MetOH (v/v) for 5 min, incubated for 1 h with the primary antibody anti-MyHC 1/200 (Millipore clone A4.1025) in PBS, 1% horse serum at room temperature, and incubated for 30 min with the secondary antibody 1/1000 Alexa488 anti-mouse IgG (Life Tech. A-10680) and Hoeschst 33342 in PBS, 1% horse serum at room temperature. Stained cells were imaged using the ImageXpress (Molecular Devices) and quantification was carried out using the MetaXpress software.

Immunohistochemistry and Image Analysis

Muscle were collected and frozen in isopentane cooled with liquid nitrogen, Muscle sections were cut at 10 um, and frozen. eMHC antibody was purchased from DSHB (# DSHB, F1.652). Laminin was used to distinguish muscle fibers, and was purchased from Sigma (# L9393). For eMHC/Laminin staining, muscle sections were thawed and blocked for 1 h in PBS, 4% BSA, 1% fetal bovine serum. Sections were then incubated in primary antibodies during 3 h at room temperature in the blocking solution, washed and incubated during 1 h at room temperature in secondary antibodies, Sections were then counterstained in Hoeschst 33342 in PBS. Stained sections were imaged using the Olympus Slide Scanner and eMHC+ fibers were manually quantified using the VS120 software.

Statistical Analysis

For qPCR or serum level analysis, statistical significance was assessed using the Student's t-test for binary comparisons. For comparison of more than 2 groups, one-way ANOVA followed by Bartlett's and Bonferroni's Multiple Comparison tests were used. All data are expressed as mean value+/−s.e.m.; and n>5. A p-value smaller than 5% was considered statistically significant. For in vitro analyses, statistical significance was assessed by the paired Student's t-test for binary comparisons. For comparison of 3 groups, one-way ANOVA followed by Bartlett's and Bonferroni's Multiple Comparison tests were used. When several replicates are represented, two-way ANOVA followed by Bonferroni's post-test were used. All data are expressed as mean value+/−s.e.m. A p-value smaller than 5% was considered statistically significant.

Results

Figure 1B:
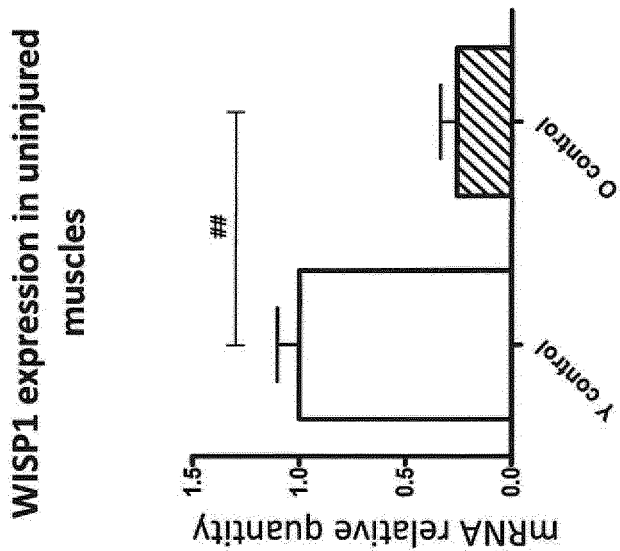
Figure 1B:
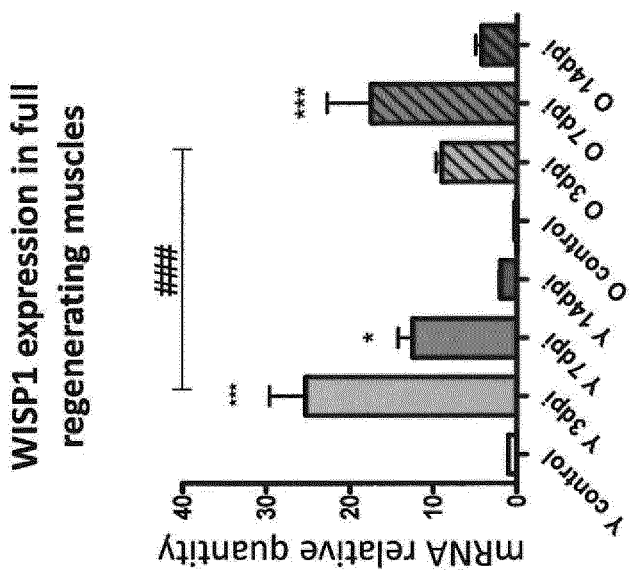
Figure 1C:
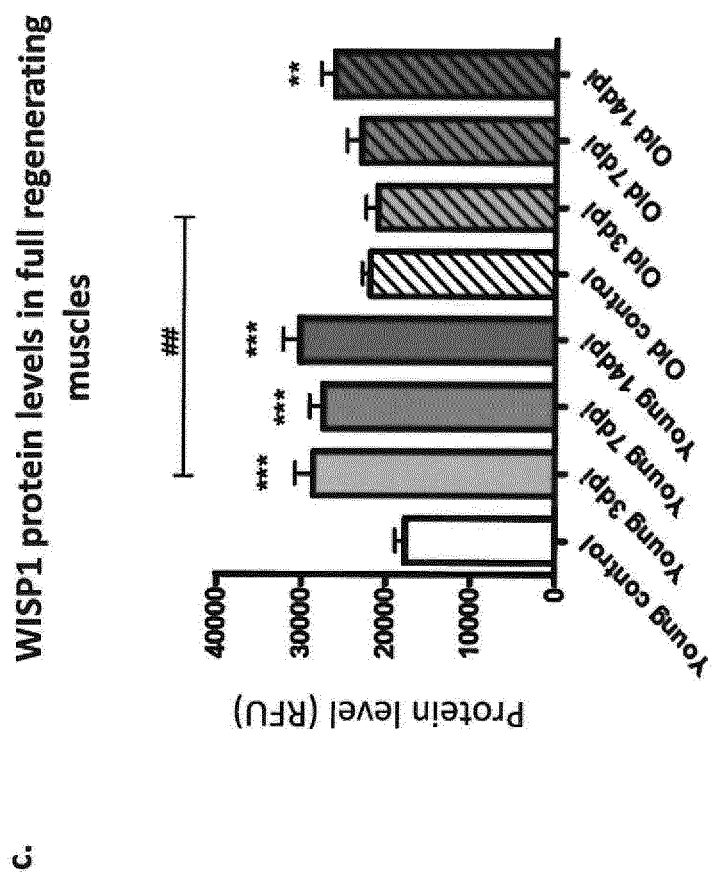
Figure 1D:
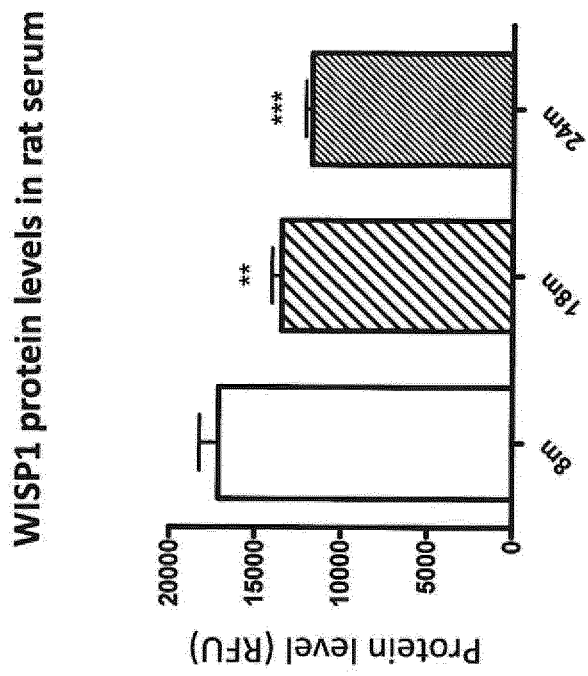

We used a model of glycerol-induced muscle injury to damage muscles from young and old mice, and activate muscle progenitors (SATs, FAPs, PDGFRα− mesenchymal cells, CD31+ endothelial cells). Those muscle resident cells, as well as the cells invading muscles after injury (CD45+, CD11b+ cells, or so called lineage cells), were then isolated in their activated state and compared to cells isolated from uninjured muscles (in their quiescent state). We showed that WISP1 was strongly upregulated in SATs, FAPs and PDGFRα− mesenchymal cells upon activation, with dominant expression in FAPs (FIG. 1a). However, WISP1 expression by FAPs upon activation was significantly reduced with age. At the full muscle level, WISP1 was also strongly upregulated a few days after injury at the mRNA and protein level, with a significant impairment in old muscles; suggesting an important role for WISP1 in muscle repair (FIG. 1b and FIG. 1c). In addition, WISP1 was also found to be down-regulated in healthy muscles with age, potentially suggesting a role for WISP1 in muscle mass maintenance with age (FIG. 1b, right graph). In rats, WISP1 was found in the circulating plasma and its content significantly decreased with age (FIG. 1d) Altogether, these results indicate a singular role for WISP1 in muscle function with age.

Figure 2:
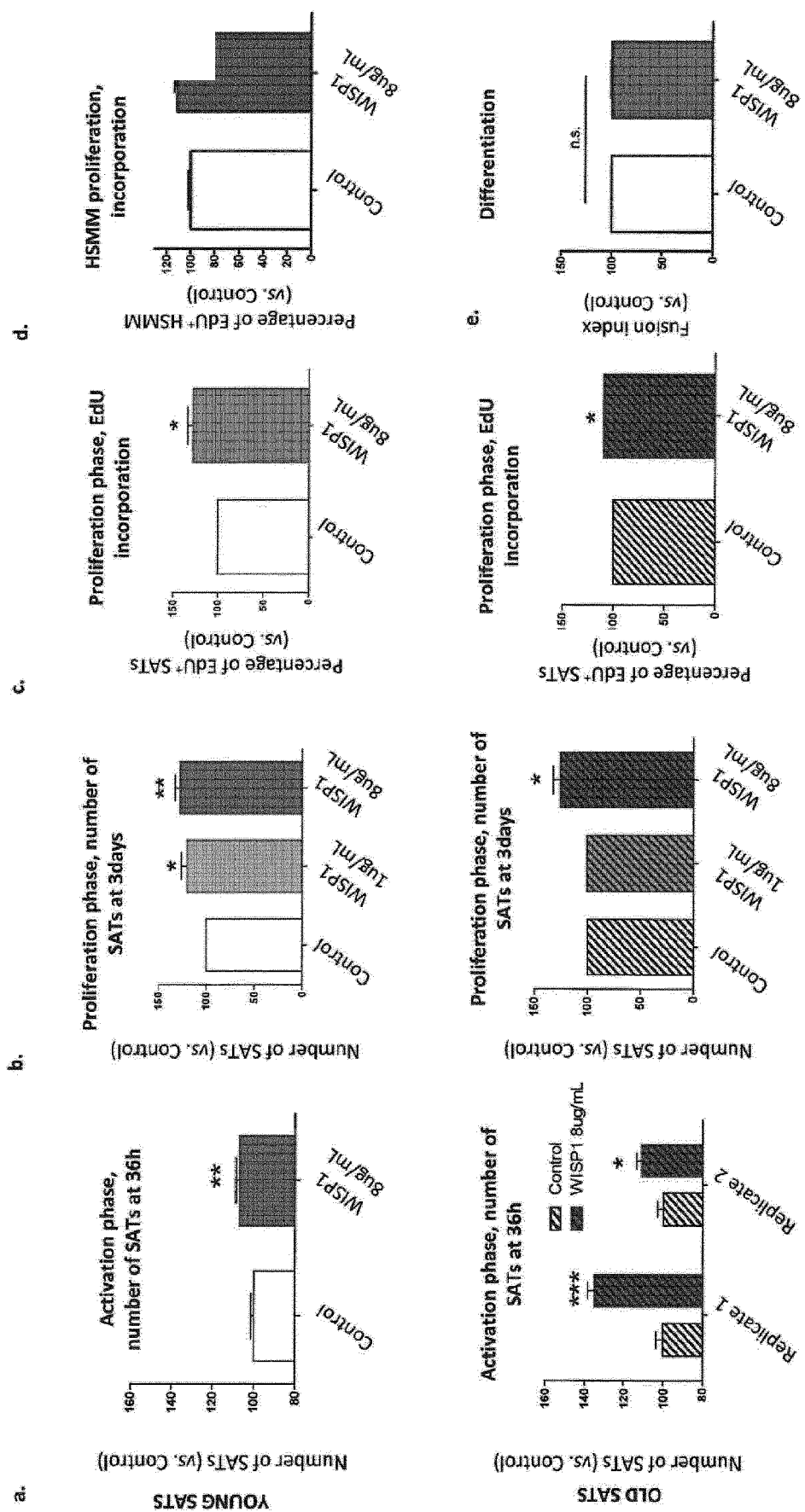

As satellite cells are the quintessential muscle stem cells responsible for muscle regeneration, we next wanted to assess whether WISP1, which is secreted in the muscle stem cell niche, could regulate satellite cell function. We thus isolated satellite cells from young and old non-injured muscles, and allowed them to adhere, activate and proliferate ex vivo upon mouse recombinant WISP1 (mrWISP1) (FIG. 2a-c). After 36 h, satellite cell numbers were significantly increased by WISP1 treatment, both in young and old cells, suggesting a role for WISP1 in satellite cell adhesion and survival (FIG. 2a)). WISP1 also demonstrated significant positive effect on satellite cell proliferation (FIG. 2b,c), as well as on human muscle progenitor proliferation (FIG. 2d). Lastly, WISP1 had no effect on muscle cell differentiation (FIG. 2e).

Thus, WISP1 is a novel muscle-secreted protein during muscle regeneration, the expression of which is lost with age. WISP1 is able to ameliorate the function of muscle stem cells, without affecting their differentiation capacities.

Figure 3:
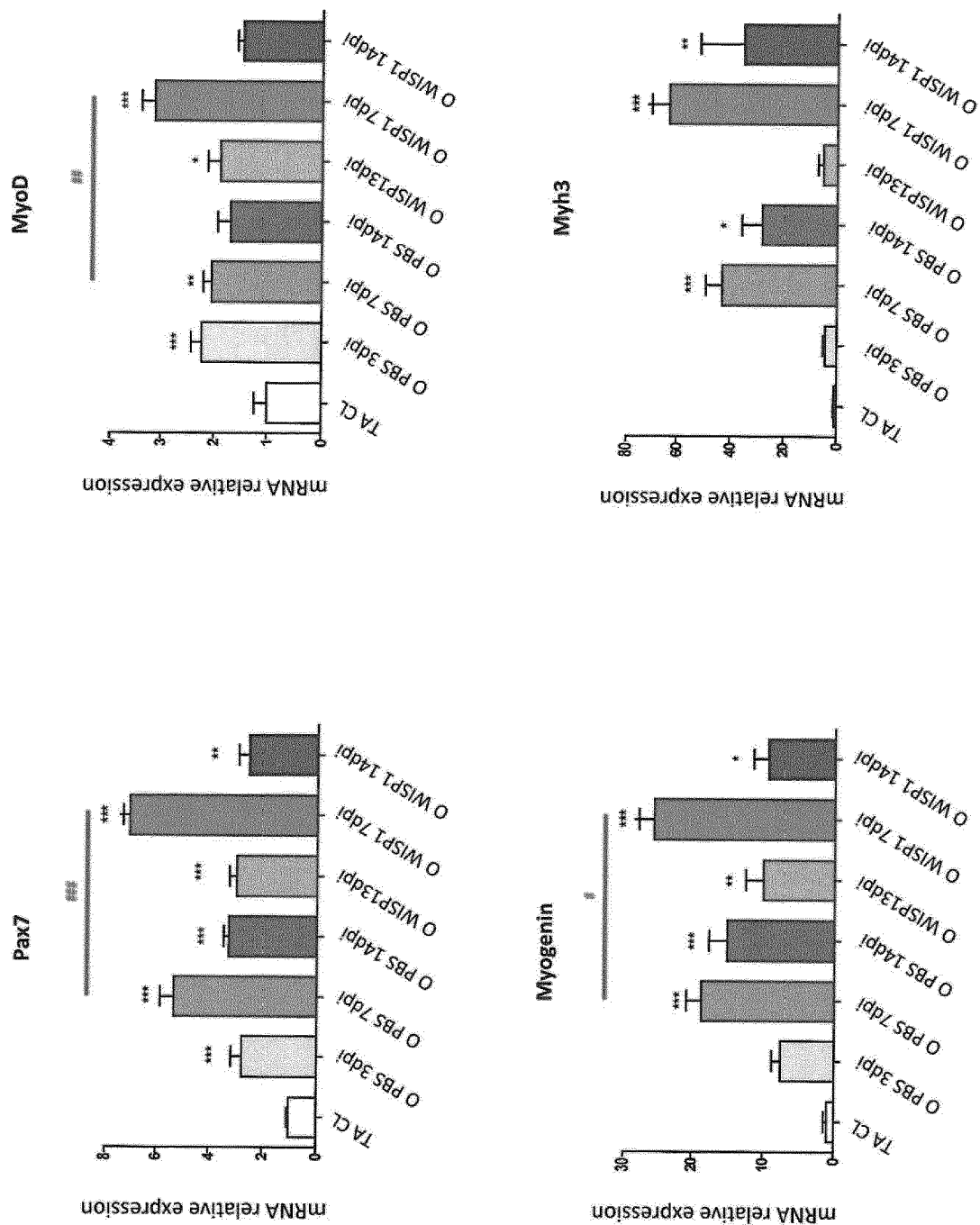
Figure 4:
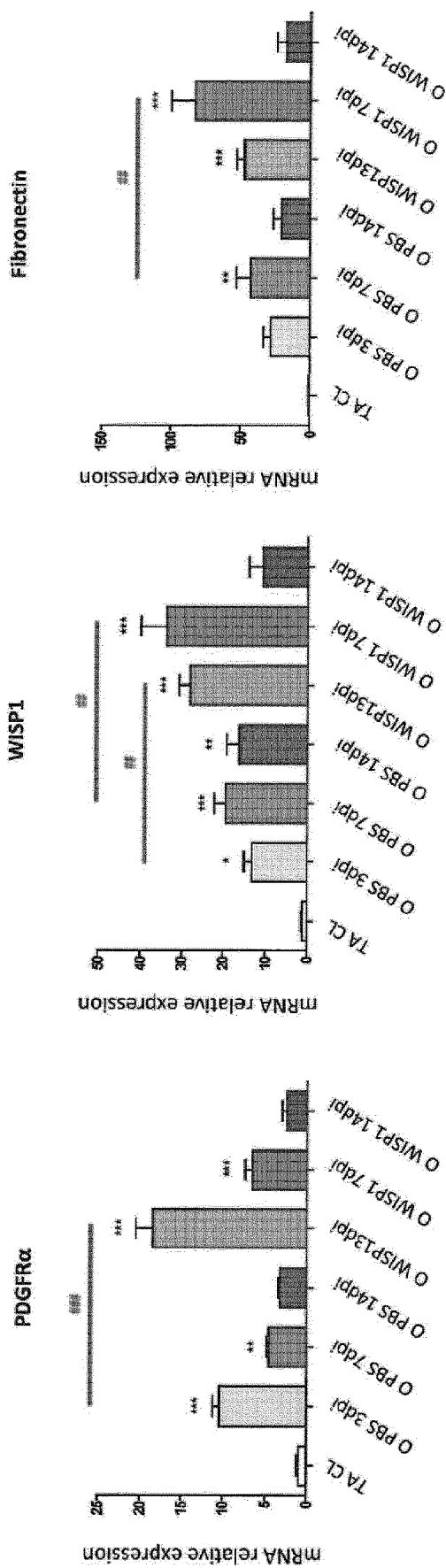

In vivo, we showed that old mice treated daily with mouse recombinant WISP1 protein after muscle damage presented a significantly higher upregulation of myogenic markers (Pax7, marker of satellite cells; MyoD, marker of activated satellite cells; myogenin, marker of differentiating satellite cells; and Myh3, marker of newly formed fibres) seven days after injury (FIG. 3). This suggested that WISP1 enhanced activation of satellite cells in vivo, and thus ameliorated the myogenic program entry. In addition, WISP1 treated muscles showed increased levels of PDGFRα, the markers of FAPs, which play a supportive role to satellite cells within the niche (Joe, A. W. et al. (2010) Nat. Cell Biol. 12: 153-63; and Murphy, M. M. et al. (2011) Development 138: 3625-37) (FIG. 4). Fibronectin was also significantly elevated in WISP1-treated muscle, possibly potentiating the beneficial effect of fibronectin on muscle stem cell function (Bentzinger, C. F. et al. (2013) Cell Stem Cell 12: 75-87). Lastly, it is possible that WISP1 is regulated through a positive feedback loop, as WISP1 endogenous expression was also increased in WISP1 treated muscles (FIG. 4). The autoregulation of WISP1 expression has already been shown in neurons and thus might also take place in skeletal muscle (Wang, S. et al. (2012) Curr. Neurovasc. Res. 9: 91-101).

Figure 5:
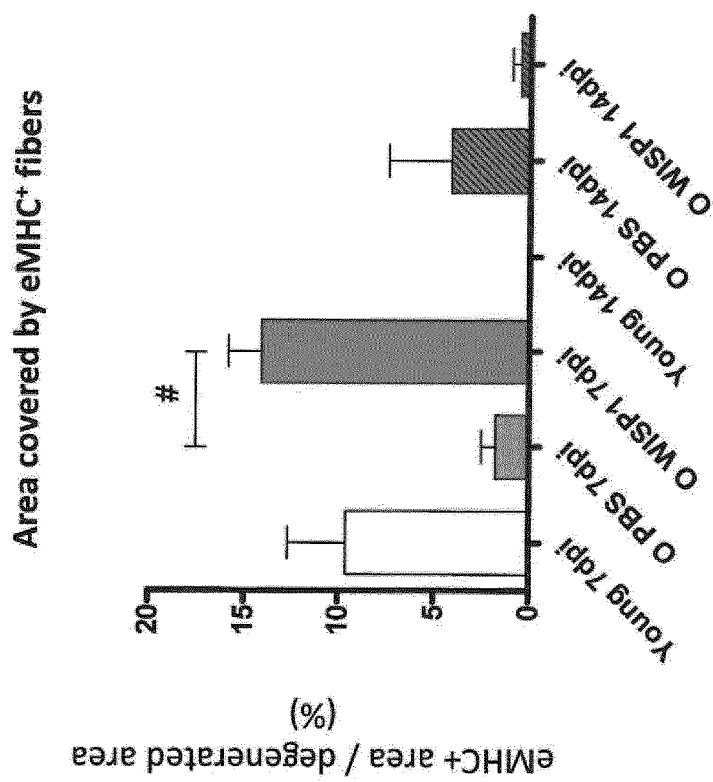

At the histological level, WISP1 treatment of old mice allowed to speed up eMHC expression, a marker of newly formed regenerating fibers, to the same levels than in young mice 7 days post muscle injury (7 dpi), suggesting an acceleration of muscle regeneration (FIG. 5). Conversely, at late timepoints of muscle regeneration (14 dpi), the proportion of regenerating fibers expressing eMHC+ was higher in old control muscle, suggesting a delay in fiber maturation as compared to young muscles, and rescued in old muscles treated with WISP1.

All publications mentioned in the above specification are herein incorporated by reference. Various modifications and variations of the described compounds, compositions, uses and methods of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention, which are obvious to those skilled in biochemistry and biotechnology or related fields, are intended to be within the scope of the following claims.

The invention claimed is:

1. A method for maintaining or increasing muscle function and/or mass and/or substantially preventing or reducing muscle wasting in a subject in need thereof, comprising administering to a subject (i) a Wnt-inducible signalling protein 1 (WISP1) or (ii) a fragment or variant thereof comprising an amino acid sequence that has at least 95% identity to SEQ ID NO: 1 or 3.

2. The method according to claim 1, wherein the WISP1 or fragment or variant thereof maintains or increases muscle mass.

3. The method according to claim 1, wherein the subject requires treating or preventing sarcopenia, frailty and/or muscle injury.

4. The method according to claim 1, wherein the subject is a human subject over the age of 30 years.

5. The method according to claim 1, wherein the subject has incurred muscle injury through a surgical intervention and/or trauma and/or as a side effect to chemical exposure to drugs or toxins.

6. The method according to claim 1, wherein the subject is to undergo a planned surgical intervention.

7. The method according to claim 1, wherein the WISP1 fragment or variant:
   (a) lacks the VWC, TSP1 and CT domains;
   (b) lacks the IGFB and VWC domains; or
   (c) consists of the CT domain.

8. The method according to claim 1, wherein the fragment or variant comprises an amino acid sequence that has at least 97% identity to SEQ ID NO: 1 or 3.

9. The method according to claim 1, wherein the fragment or variant comprises an amino acid sequence that has at least 99% identity to SEQ ID NO: 1 or 3.

10. The method according to claim 1, wherein the fragment or variant comprises an amino acid sequence that has 100% identity to SEQ ID NO: 1 or 3.

11. The method according to claim 1, wherein the fragment or variant comprises an amino acid sequence that has 100% identity to SEQ ID NO: 1.

12. The method according to claim 1, wherein the method comprises administering to the subject the Wnt-inducible signalling protein 1 (WISP1).

* * * * *